(12) United States Patent
Kalkum et al.

(10) Patent No.: US 10,520,496 B2
(45) Date of Patent: Dec. 31, 2019

(54) METHODS, COMPOSITIONS, AND KITS FOR DETECTION OF BACTERIAL PROTEASES

(71) Applicant: CITY OF HOPE, Duarte, CA (US)

(72) Inventors: Markus Kalkum, Azusa, CA (US); Ismail Al-Abdullah, Monrovia, CA (US)

(73) Assignee: CITY OF HOPE, Duarte, CA (US)

( * ) Notice: Subject to any disclaimer, the term of this patent is extended or adjusted under 35 U.S.C. 154(b) by 31 days.

(21) Appl. No.: 15/895,969

(22) Filed: Feb. 13, 2018

(65) Prior Publication Data
US 2019/0004036 A1 Jan. 3, 2019

Related U.S. Application Data

(63) Continuation of application No. PCT/US2016/046945, filed on Aug. 13, 2016.

(60) Provisional application No. 62/204,947, filed on Aug. 13, 2015.

(51) Int. Cl.
| | | |
|---|---|---|
| *G01N 33/52* | (2006.01) | |
| *G01N 33/542* | (2006.01) | |
| *C12N 9/52* | (2006.01) | |
| *C12N 9/64* | (2006.01) | |
| *G01N 33/573* | (2006.01) | |
| *G01N 33/58* | (2006.01) | |

(52) U.S. Cl.
CPC .............. *G01N 33/542* (2013.01); *C12N 9/52* (2013.01); *C12N 9/6491* (2013.01); *C12N 9/6494* (2013.01); *G01N 33/573* (2013.01); *G01N 33/582* (2013.01)

(58) Field of Classification Search
None
See application file for complete search history.

(56) References Cited

U.S. PATENT DOCUMENTS

| | | |
|---|---|---|
| 5,589,171 A | 12/1996 | Wegman |
| 7,087,164 B2 | 8/2006 | Tubbs et al. |

FOREIGN PATENT DOCUMENTS

WO    WO-2016193181 A1 * 12/2016

OTHER PUBLICATIONS

Bagramyan, K., et al., "Attomolar Detection of Botulinum Toxin Type A in Complex Biological Matrices," PLoS ONE 3(4):e2041 (2008).
Baici, A., et al., "A Handy Assay for Collagenase Using Reconstituted Fluorescein-Labeled Collagen Fibrils," Anal. Biochem. 108:230-232 (1980).
Balamurugan, A. N., et al., "Harmful Delayed Effects of Exogenous Isolation Enzymes on Isolated Human Islets: Relevance to Clinical Transplantation," Am. J. Transplant. 5:2671-2681 (2005).
Balamurugan, A. N., et al., "Suitability of Human Juvenile Pancreatic Islets for Clinical Use," Diabetologia 49:1845-1854 (2006).
Balamurugan, A. N., et al., "Islet Product Characteristics and Factors Related to Successful Human Islet Transplantation From the Collaborative Islet Transplant Registry (CITR) 1999-2010," Am. J. Transplant. 14:2595-2606 (2014).
Balamurugan, A. N., et al., "Identifying Effective Enzyme Activity Targets for Recombinant Class I and Class II Collagenase for Successful Human Islet Isolation," Transplantation Direct 2:e54 (2016).
Brandhorst, H., et al., "Successful Human Islet Isolation Utilizing Recombinant Collagenase," Diabetes 52:1143-1146 (2003).
Brandhorst, H., et al., "The Ratio Between Collagenase Class I and Class II Influences the Efficient Islet Release From the Rat Pancreas," Transplant. 85:456-461 (2008).
Brennan, D. C., et al., "Long-Term Follow-Up of the Edmonton Protocol of Islet Transplantation in the United States," Am. J. Transplant. 16:509-517 (2016).
Bucher, P., et al., "Serva Collagenase NB1: A New Enzyme Preparation for Human Islet Isolation," Transplant. Proc. 36:1143-1144 (2004).
Caballero-Corbalan, J., et al., "Vitacyte Collagenase HA: A Novel Enzyme Blend for Efficient Human Islet Isolation," Transplant. 88(12):1400-1402 (2009).
Cummings, R. T., et al., "A Peptide-Based Fluorescence Resonance Energy Transfer Assay for Bacillus Anthracis Lethal Factor Protease," PNAS 99(10):6603-6606 (2002).
Diaz, S. A., et al., "Probing the Kinetics of Quantum Dot-Based Proteolytic Sensors," Anal. Bioanal. Chem. 407:7307-7318 (2015).
Fetterhoff, T.J., et al., "Human Pancreatic Dissociation Using a Purified Enzyme Blend," Transplant. Proc. 27(6):3282-3283 (1995).
Gray, D. W. R. et al., "A Method for Isolation of Islets of Langerhans from the Human Pancreas," Diabetes 33:1055-1061 (1984).
Johnson, P.R.V., et al., "Collagenase and Human Islet Isolation," Cell Transplant. 5(4):437-452 (1996).
Kaddis, J. S., et al., "Multi-Center Analysis of Novel and Established Variables Associated with Successful Human Islet Isolation Outcomes," Am. J. Transplant. 10(3):646-656 (2010).

(Continued)

*Primary Examiner* — Fred H Reynolds
(74) *Attorney, Agent, or Firm* — Perkins Coie LLP; Lara Dueppen; Courtney Prochnow

(57) ABSTRACT

Provided herein are novel fluorogenic and bioluminescent bacterial protease substrates that contain at least one bacterial protease cleavage site. In some embodiments, the proteases that cleave the protease substrates are bacterial proteases including those used for tissue dissociation, cell isolation, and cell detachment, such as the preparation of islet cells. Additionally, the novel protease substrates described herein may be used to assess the activity of certain bacterial proteases involved in isolating primary cells and stem cells. Methods and protease detection kits using the novel protease substrates are also provided herein.

38 Claims, 26 Drawing Sheets
Specification includes a Sequence Listing.

(56) References Cited

OTHER PUBLICATIONS

Kaplan, B.E., et al., "Solid-Phase Synthesis and Characterization of Carcinoembryonic Antigen (CEA) Domains," J. Pept. Res. 52(4):249-260 (1998).

Kennedy, R. H., et al., "Pancreatic Extracellular Matrix Alterations in Chronic Pancreatitis," Pancreas 2(1):61-72 (1987).

Kin, T., et al., "Detrimental Effect of Excessive Collagenase Class II on Human Islet Isolation Outcome," Transplantation 21:1059-1065 (2008).

Kin, T., et al., "Experience of Islet Isolation Without Neutral Protease Supplementation," Islets 2(5):278-282 (2010).

Linetsky, E., et al., "Comparison of Collagenase Type P and Liberase During Human Islet Isolation Using the Automated Method," Transplant. Proc. 27(6):3264 (1995).

Linetsky, E., et al., "Improvde Human Islet Isolation Using a New Enzyme Blend, Liberase," Diabetes 46:1120-1123 (1997).

Matayoshi, E. D., et al., "Novel Fluorogenic Substrates for Assaying Retroviral Proteases by Resonance Energy Transfer," Science 247:954-958 (1990).

Matsushita, O., et al., "Gene Duplication and Multiplicity of Collagenases in Clostridium Histolyticum," J. Bacteriol. 181(3):923-933 (1999).

McCarthy, R.C., et al., "Development and Characterization of a Collagen Degradation Assay to Assess Purified Collagenase Used in Islet Isolation," Transplant. Proc. 40:339-342 (2008).

Meier, R. P. H., et al., "Islet of Langerhans Isolation from Pediatric and Juvenile Donor Pancreases," Transplant Int. 27:949-955 (2014).

Nano, R., et al., "Islet Isolation for Allotransplantation: Variables Associated with Successful Islet Yield and Graft Function," Diabetologia 48:906-912 (2005).

Orr, C., et al., "Quantifying Insulin Therapy Requirements to Preserve Islet Graft Function Following Islet Transplantation," Cell Transplant. 23:85-95 (2016).

Qi, M., et al., "Five-year Follow-up of Patients with Type 1 Diabetes Transplanted with Allogeneic Islets: The UIC Experience," Acta Diabetol. 51(5):833-843 (2014).

Qi, M., et al., "The Choice of Enzyme for Human Pancreas Digestion Is a Critical Factor for Increasing the Success of Islet Isolation," Transplant. Direct 1:e14 (2015).

Saikumari, Y. K., et al., "An Internally Quenched Fluorescent Substrate for Collagenase," Biopolymers Peptide Science 90(2):131-137 (2008).

Salamone, M., et al., "A New Method to Value Efficiency of Enzyme Blends for Pancreatic Tissue Digestion," Transplant. Proc. 42:2043-2048 (2010).

Standard Protein Blast, retrieved from http://blast.ncbi.nlm.nih.gov/Blast.cgi?PAGE=Proteins on Mar. 21, 2018.

Szot, G. L., et al., "Successful Clinical Islet Isolation Using a GMP-Manufactured Collagenase and Neutral Protease," Transplant. 88(6):753-756 (2009).

Tokmina-Roszyk, M., et al., "Development of a Fluorescence Resonance Energy Transfer Assay for Monitoring Bacterial Collagenase Triple-Helical Peptidase Activity," Anal. Biochem. 453:61-69 (2014).

The Uniprot Consortium, Uniprot Knowledge Base, retrieved from http://www.uniprot.org/ on Mar. 21, 2018.

Uscanga, L., et al., "Immunolocalization of Collagen Types, Laminin and Fibronectin in the Normal Human Pancreas," Digestion 30:158-164 (1984).

Van Wart, H. E., et al., "Complementary Substrate Specificities of Class I and Class II Collagenases from *Clostridium histolyticum*," Biochem. 24:6520-6526 (1985).

Voss, E. W., et al., "Detection of Protease Activity Using a Fluorescence-Enhancement Globular Substrate," BioTechniques 20:286-291 (1996).

Weimer, S., et al., "A Quenched Fluorescent Dipeptide for Assaying Dispase-and Thermolysin-Like Proteases," Anal. Biochem. 352:110-119 (2006).

Wu, Q., et al., "Purification and Characterization of a Novel Collagenase from *Bacillus pumilus* Col-J," Appl. Biochem. Biotechnol. 160:129-139 (2010).

Wunsch, E., et al., "On the Quantitative Determination of Collagenase," Hoppe Seylers Z Physiol. Chem. 333: 149-151 (1963).

Yamamoto, T., et al., "Deterioration and Variability of Highly Purified Collagenase Blends Used in Clinical Islet Isolation," Transplantation 84:997-1002 (2007).

* cited by examiner

5FAMcollagenPPT

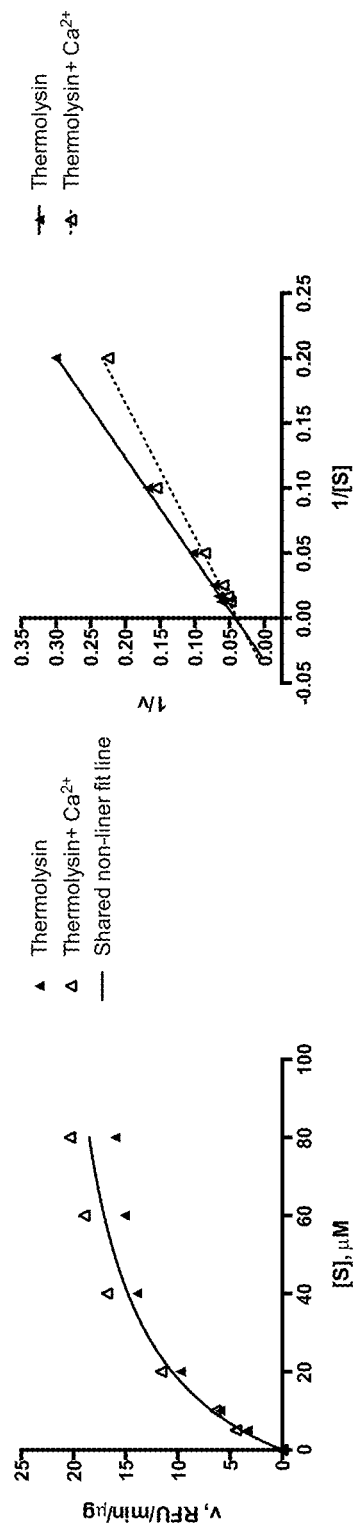
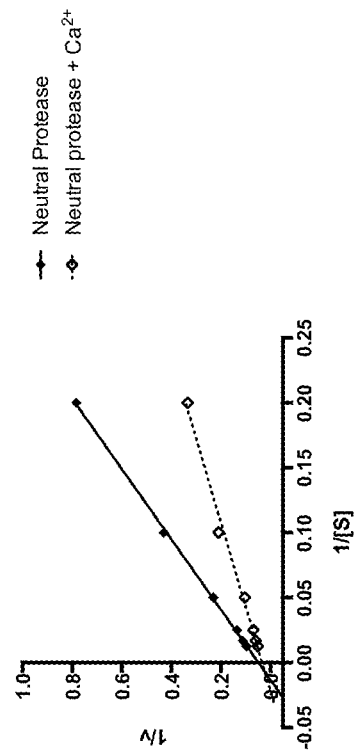
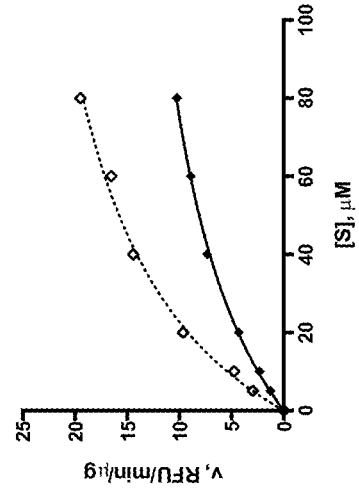
Fig. 4E, Fig. 4F, Fig. 4G, Fig. 4H

Fig.5

| Enzymes | Vmax (RFU/min/ug) | Km (uM) |
|---|---|---|
| Collagenase I | 808.8 ± 59.5 | 24.7 ± 4.8 |
| Collagenase I + CaCl2 | 1845.0 ± 226.0 | 36.7 ± 10.2 |
| Collagenase II | 2676.0 ± 149.6 | 14.9 ± 2.7 |
| Collagenase II + CaCl2 | 2802 ± 276 | 19.9 ± 5.6 |
| Thermolysin | 21.3 ± 0.6 | 24.1 ± 1.7 |
| Thermolysin + CaCl2 | 28.2 ± 9.3 | 29.2 ± 23.8 |
| Neutral Protease | 18.8 ± 3.9 | 65.6 ± 24.5 |
| Neutral Protease + CaCl2 | 30.3 ± 11.0 | 46.0 ± 34.9 |

Fig. 15

SEQ ID NO: 1

Ala-Gly-Gly-Pro-Leu-Gly-Pro-Pro-Gly-Pro-Gly-Gly

SEQ ID NO: 2

5-FAM-Ala-Gly-Gly-Pro-Leu-Gly-Pro-Pro-Gly-Pro-Gly-Gly-Lys[DABCYL]-amide

Fig. 16

SEQ ID NO: 3

ATGAGCGATAAAATTATTCACCTGACTGACGACAGTTTTGACACGGATGTACTCAA
AGCGGACGGGGCGATCCTCGTCGATTTCTGGGCAGAGTGGTGCGGTCCGTGCAA
AATGATCGCCCCGATTCTGGATGAAATCGCTGACGAATATCAGGGCAAACTGACC
GTTGCAAAACTGAACATCGATCAAACCCTGGCACTGCGCCGAAATATGGCATCC
GTGGTATCCCGACTCTGCTGCTGTTCAAAAACGGTGAAGTGGCGGCAACCAAAGT
GGGTGCACTGTCTAAAGGTCAGTTGAAAGAGTTCCTCGACGCTAACCTGGCCGGT
TCTGGTTCTGGCCATATGCACCATCATCATCATCATTCTTCTGGTCTGGTGCCACG
CGGTTCTGGTATGAAAGAAACCGCTGCTGCTAAATTCGAACGCCAGCACATGGAC
AGCCCAGATCTGGGTACCGACGACGACGACAAGGCCATGGCGATATCGGATCCG
AATTCGGCCGGTGGTCCGCTGGGTCCGCCGGGTCCGGGTGGTGCCGGTGGTCC
GCTGGGTCCGCCGGGTCCGGGTGGTACCAGCAAAGTTTATGATCCGGAACAGCG
TAAACGTATGATTACCGGTCCGCAGTGGTGGGCACGTTGTAAACAAATGAATGTTC
TGGACTCCTTCATCAACTATTACGATAGCGAAAACATGCCGAAAACGCCGTTATTT
TTCTGCATGGTAATGCAGCAAGCAGCTATCTGTGGCGTCATGTTGTTCCGCATATT
GAACCGGTTGCCCGTTGTATTATTCCGGATCTGATTGGTATGGGTAAAAGCGGTAA
ATCAGGTAATGGTAGCTATCGTCTGCTGGATCATTACAAATATCTGACCGCATGGT
TTGAACTGCTGAATCTGCCGAAAAAAATCATCTTTGTTGGTCATGATTGGGGTGCAT
GTCTGGCATTTCATTATAGCTATGAACACCAGGACAAAATCAAAGCCATTGTTCATG
CGGAAAGCGTTGTTGATGTTATTGAAAGCTGGGATGAATGGCCTGATATCGAAGAA
GATATTGCCCTGATTAAAAGCGAAGAGGGTGAAAAAATGGTGCTGGAAAACAACTT
TTTTGTGGAAACCGTTCTGCCGAGCGTTATTATGCGTAAACTGGAACCGGAAGAAT
TGCAGCATATCTGGAACCGTTTAAAGAAAAGGTGAAGTTCGTCGTCCGACCCTG
AGCTGGCTGCGTGAAATTCCGCTGGTTAAAGGTGGTAAACCGGATGTTGTTCAGAT
TGTGCGTAACTATAATGCATATCTGCGTGCAAGTGATGACCTGCCTAAAATGTTTAT
CGAAAGCGATCCGGGTTTTTTTAGCAACGCAATTATTGAGGGTGCCAAAAAATTCC
CGAATACCGAATTTGTGAAAGTGAAAGGTCTGCACTTTAGCCAAGAGGATGCACCG
GATGAAATGGGCAAATATATCAAAAGCTTTGTGGAACGCGTGCTGAAAAATGAACA
GCTCGAGCACCACCACCACCACCACTGA

Fig. 17

SEQ ID NO: 4

MSDKIIHLTDDSFDTDVLKADGAILVDFWAEWCGPCKMIAPILDEIADEYQGKLTVAKLN
IDQNPGTAPKYGIRGIPTLLLFKNGEVAATKVGALSKGQLKEFLDANLAGSGSGHMHH
HHHHSSGLVPRGSGMKETAAAKFERQHMDSPDLGTDDDDKAMAISDPNS**AGGPLGP
PGPGGAGGPLGPPGPGG**TSKVYDPEQRKRMITGPQWWARCKQMNVLDSFINYYDS
EKHAENAVIFLHGNAASSYLWRHVVPHIEPVARCIIPDLIGMGKSGKSGNGSYRLLDHY
KYLTAWFELLNLPKKIIFVGHDWGACLAFHYSYEHQDKIKAIVHAESVVDVIESWDEWP
DIEEDIALIKSEEGEKMVLENNFFVETVLPSVIMRKLEPEEFAAYLEPFKEKGEVRRPTL
SWLREIPLVKGGKPDVVQIVRNYNAYLRASDDLPKMFIESDPGFFSNAIIEGAKKFPNTE
FVKVKGLHFSQEDAPDEMGKYIKSFVERVLKNEQLEHHHHHH

METHODS, COMPOSITIONS, AND KITS FOR DETECTION OF BACTERIAL PROTEASES

PRIORITY CLAIM

This application is a continuation of International Application No. PCT/US2016/046945, filed Aug. 13, 2016, which claims the benefit of U.S. Provisional Application No. 62/204,947, filed Aug. 13, 2015, which is incorporated herein in its entirety, including drawings.

BACKGROUND

Islet isolation from human pancreata for clinical treatment of type 1 diabetes requires bacterial enzymes such as collagenase, thermolysin, and neutral protease to digest the organ and to free the islets from exocrine tissues. However, the quality of collagenase in terms of variability between manufacturers and from lot to lot is a major problem that limits the use of islet transplantation. Thus, there is a need to develop precise and sensitive substrates to evaluate and quantify the activity of bacterial proteases that are critical for the digestion of pancreata to free islets without compromising their quality or quantity. Bacterial proteases are not only relevant for pancreas digestion and enhanced isolation of islets, but also for other tissue dissociation, cell isolation, and cell detachment applications, such as those used to isolate primary cells and stem cells. Therefore, specific and sensitive substrates to assess the activity of certain bacterial proteases may also be useful for isolating primary cells and stem cells. Additionally, these specific and sensitive substrates would also be useful in measuring the activity of bacterial proteases, such as collagenase, which may be used in certain drugs to treat diseases such as those that involve an excess of inelastic collagen (see, e.g., U.S. Pat. No. 5,589,171). Thus, there is a need for specific and sensitive substrates to measure the activity of bacterial proteases, so that appropriate dosage, concentration and/or activity can be determined and used for specific in vitro and in vivo applications.

SUMMARY

Provided herein in certain embodiments are novel fluorogenic and bioluminescent protease substrates for prokaryotic protease detection. Also provided herein are methods and kits using the novel protease substrates. Provided herein in certain embodiments are fluorogenic protease substrates comprising a donor fluorophore, an acceptor having an absorbance spectrum overlapping the emission spectrum of the donor fluorophore, and one or more amino acid sequences comprising at least one bacterial protease cleavage site, the amino acid sequence comprising, consisting of, or consisting essentially of Ala-Gly-Gly-Pro-Leu-Gly-Pro-Pro-Gly-Pro-Gly-Gly (i.e., SEQ ID NO: 1). In certain embodiments, the donor fluorophore may be one or more fluorophores conjugated at or near the N-terminus of the protease substrate and the acceptor is a DABYCL conjugated at or near the C-terminus of the protease substrate. In certain embodiments, the fluorogenic protease substrate may comprise, consist of, or consist essentially of [5-Fam]-Ala-Gly-Gly-Pro-Leu-Gly-Pro-Pro-Gly-Pro-Gly-Gly-Lys-[DABYCL]-amide (i.e., SEQ ID NO: 2). In certain embodiments, the bacterial protease cleavage site may be a collagenase cleavage site. In certain embodiments, the fluorogenic protease substrate may be resistant to cleavage by trypsin, chymotrypsin and elastase.

Provided herein in certain embodiments are methods for detecting the presence of one or more bacterial proteases in a sample comprising exposing the sample putatively containing the one or more bacterial proteases to an enrichment matrix comprising a fluorogenic protease substrate that is capable of eliciting a detectable fluorescence signal when modified by the one or more bacterial proteases, the fluorogenic protease substrate comprising one or more amino acid sequences comprising at least one bacterial protease cleavage site, the amino acid sequence comprising, consisting of, or consisting essentially of Ala-Gly-Gly-Pro-Leu-Gly-Pro-Pro-Gly-Pro-Gly-Gly (i.e., SEQ ID NO: 1), measuring the level of change in the detectable fluorescence signal, and detecting the presence of the one or more bacterial proteases when the level of change in the detectable fluorescence signal in the sample is elevated. In certain embodiments, the fluorogenic protease substrate may comprise, consist of, or consist essentially of [5-Fam]-Ala-Gly-Gly-Pro-Leu-Gly-Pro-Pro-Gly-Pro-Gly-Gly-Lys-[DABYCL]-amide (i.e., SEQ ID NO: 2). In certain embodiments, the one or more bacterial proteases may be used for the preparation of islet cells. In certain embodiments, the one or more bacterial proteases may be used for isolating primary cells or stem cells. In certain embodiments, the one or more bacterial proteases may comprise one or more of class I collagenase, class II collagenase, thermolysin, neutral protease, and dispase. In certain embodiments, the enrichment matrix may further comprise a protease substrate specific antibody that binds the fluorogenic protease substrate in the sample. In certain embodiments, the protease substrate specific antibody may bind a region of the fluorogenic protease substrate wherein, if the region of the fluorogenic protease substrate is a fluorophore, the antibody may be an anti-fluorescein antibody; if the region of the fluorogenic protease substrate is an acceptor, the antibody may be an anti-DABYCL antibody; and if the region of the fluorogenic protease substrate is one or more amino acids of the fluorogenic protease substrate amino acid sequence, the antibody may be a sequence specific antibody.

In certain embodiments, the fluorogenic protease substrate may be resistant to cleavage by trypsin, chymotrypsin and elastase. In certain embodiments, the enrichment matrix may be provided in one or more columns.

Also provided herein are bacterial protease detection kits comprising an enrichment matrix comprised of one or more affinity beads to which one or more fluorogenic protease substrates comprising a donor fluorophore, an acceptor having an absorbance spectrum overlapping the emission spectrum of the donor fluorophore, and one or more amino acid sequences comprising at least one bacterial protease cleavage site, the amino acid sequence comprising, consisting of, or consisting essentially of Ala-Gly-Gly-Pro-Leu-Gly-Pro-Pro-Gly-Pro-Gly-Gly (i.e., SEQ ID NO: 1), wherein a detectable fluorescence signal is produced upon interaction of the substrate with a bacterial protease. In certain embodiments, the amino acid sequence may comprise, consist of, or consist essentially of [5-Fam]-Ala-Gly-Gly-Pro-Leu-Gly-Pro-Pro-Gly-Pro-Gly-Gly-Lys-[DABYCL]-amide (i.e., SEQ ID NO: 2). In certain embodiments, the bacterial protease may comprise one or more of class I collagenase, class II collagenase, thermolysin, neutral protease, and dispase. In certain embodiments, the enrichment matrix may further comprise a fluorogenic substrate specific antibody that binds a region of the fluorogenic protease substrate in the sample.

In certain embodiments, if the region of the fluorogenic protease substrate is the fluorophore, the antibody may be an anti-fluorescein antibody, if the region of the fluorogenic protease substrate is the acceptor, the antibody may be an anti-DABYCL antibody, and if the region of the fluorogenic protease substrate is one or more amino acids of the fluorogenic protease substrate amino acid sequence, the antibody may be a sequence-specific antibody. In certain embodiments, the fluorogenic protease substrate may be resistant to cleavage by trypsin, chymotrypsin and elastase.

Provided herein in certain embodiments are bioluminescent protease substrates comprising one or more luciferase proteins or fragments thereof and one or more amino acid sequences comprising at least one bacterial protease cleavage site, the amino acid sequence comprising Ala-Gly-Gly-Pro-Leu-Gly-Pro-Pro-Gly-Pro-Gly-Gly (i.e., SEQ ID NO: 1). In certain embodiments, the bioluminescent protease substrate may further comprise one or more selected from a positive control cleavage site, an affinity tag, and a linker. In certain embodiments, the bioluminescent protease substrate may comprise, consist of, or consist essentially of SEQ ID NO: 4. In certain embodiments, the bacterial protease cleavage site may be one or more collagenase cleavage sites.

Provided herein in certain embodiments are methods for detecting the presence of one or more bacterial proteases in a sample comprising exposing the sample putatively containing the one or more bacterial proteases to an enrichment matrix comprising a bioluminescent protease substrate that is capable of eliciting a detectable luminogenic signal when modified by the one or more bacterial proteases, the bioluminescent protease substrate comprising one or more luciferase proteins or fragments thereof and one or more amino acid sequences comprising at least one bacterial protease cleavage site, the amino acid sequence comprising Ala-Gly-Gly-Pro-Leu-Gly-Pro-Pro-Gly-Pro-Gly-Gly (i.e., SEQ ID NO: 1), measuring the level of change in the detectable luminogenic signal, and detecting the presence of the one or more bacterial proteases when the level of change in the detectable luminogenic signal in the sample is elevated. In certain embodiments, the bioluminescent protease substrate may further comprise one or more selected from a positive control cleavage site, an affinity tag, and a linker. In certain embodiments, the bioluminescent protease substrate may comprise, consist of, or consist essentially of SEQ ID NO: 4. In certain embodiments, the one or more bacterial proteases may be used for the preparation of islet cells. In certain embodiments, the one or more bacterial proteases may be used for isolating primary cells or stem cells. In certain embodiments, the one or more bacterial proteases may comprise one or more of class I collagenase, class II collagenase, thermolysin, neutral protease, and dispase. In certain embodiments, the enrichment matrix may further comprise a protease substrate specific antibody that binds the bioluminescent protease substrate in the sample. In certain embodiments, the enrichment matrix may be provided in one or more columns.

Also provided herein are bacterial protease detection kits comprising an enrichment matrix comprising one or more bioluminescent protease substrates comprising one or more luciferase proteins or fragments thereof and one or more amino acid sequences comprising at least one bacterial protease cleavage site, the amino acid sequence comprising, consisting of, or consisting essentially of Ala-Gly-Gly-Pro-Leu-Gly-Pro-Pro-Gly-Pro-Gly-Gly (i.e., SEQ ID NO: 1), wherein a detectable fluorescence signal is produced upon interaction of the substrate with the bacterial protease. In certain embodiments, the bioluminescent protease substrate may further comprise one or more selected from a positive control cleavage site, an affinity tag, and a linker. In certain embodiments, the bioluminescent protease substrate may comprise, consist of, or consist essentially of SEQ ID NO: 4. In certain embodiments, the bacterial protease may comprise one or more of class I collagenase, class II collagenase, thermolysin, neutral protease, and dispase. In certain embodiments, the enrichment matrix may further comprise a protease substrate specific antibody that binds the bioluminescent protease substrate in the sample. In certain embodiments, the enrichment matrix may be provided in one or more columns.

BRIEF DESCRIPTION OF THE DRAWINGS

FIG. 3A shows a Michaelis-Menten plot for collagenase I at a concentration of 0.45 µg/ml. Collagenase I is represented by squares and collagenase I with 4.14 mM calcium is represented by triangles. FIG. 3B shows a Lineweaver-Burke plot for collagenase I at a concentration of 0.45 µg/ml. Collagenase I without calcium is represented by squares and collagenase I with 4.14 mM calcium is represented by triangles. FIG. 3C shows a Michaelis-Menten plot for collagenase II at a concentration of 0.3 µg/ml. Collagenase II without calcium is represented by squares and collagenase II with 4.14 mM calcium is represented by triangles. FIG. 3D shows a Lineweaver-Burke plot for collagenase II at a concentration of 0.3 µg/ml. Collagenase II without calcium is represented by squares and collagenase II with 4.14 mM calcium is represented by triangles. FIG. 3E shows a Michaelis-Menten plot for thermolysin at a concentration of 17 µg/ml. Thermolysin without calcium is represented by squares and thermolysin with 4.14 mM calcium is represented by triangles. FIG. 3F shows a Lineweaver-Burke plot for thermolysin at a concentration of 17 µg/ml. Thermolysin without calcium is represented by squares and thermolysin with 4.14 mM calcium is represented by triangles. FIG. 3G shows a Michaelis-Menten plot for neutral protease at a concentration of 20 µg/ml. Neutral protease without calcium is represented by squares and neutral protease with 4.14 mM calcium is represented by triangles. FIG. 3H shows a Lineweaver-Burke plot for neutral protease at a concentration of 20 µg/ml. Neutral protease without calcium is represented by squares and neutral protease with 4.14 mM calcium is represented by triangles. For each of the plots in FIGS. 3A-3H, the n value for each protease tested was 3 (n=3).

FIGS. 4A-H show plots of Michaelis-Menten (FIGS. 4A, 4C, 4E and 4G) and Lineweaver-Burk (FIGS. 4B, 4D, 4F, and 4H) double-reciprocal plots analysis of enzyme cleavage of protease substrate 5FAMcollagenPPT. The substrate was used at various concentrations (5, 10, 20, 40, 60, and 80 µM) in the presence of Collagenase I (0.45 µg/ml), Neutral Protease (20 µg/ml), Collagenase II (0.3 µg/ml), and Thermolysin (17 µg/ml). The reactions of 0.45 µg/ml of Collagenase I (n=3, FIGS. 4A,4B) and 20 µg/ml of Neutral Protease (n=3, FIGS. 4G,4H) were significantly enhanced in the presence of $CaCl_2$ (Collagenase I, p<0.0001; Neutral Protease, p<0.0001). The reaction curves of both 0.3 µg/ml of Collagenase II (n=3, FIGS. 4C,4D) and 17 µg/ml Thermolysin (n=3, FIGS. 4E,4F) did not change significantly when $CaCl_2$ was added (Collagenase II, p=0.490; Thermolysin, p=0.239), which is justified by the occurrence of shared non-liner fit line between the conditions of presence and absent of $CaCl_2$ (FIGS. 4C,4E).

FIG. 5 shows the kinetic parameters of the different enzymes that cleave the protease substrate 5FAMcollagenPPT. RFU stands for relative fluorescent unit. The values were expressed as Mean±SEM.

FIG. 10A shows a Michaelis-Menten plot for collagenase I at a concentration of 0.45 µg/ml. FIG. 10B shows a Lineweaver-Burke plot for collagenase I at a concentration of 0.45 µg/ml. FIG. 10C shows a Michaelis-Menten plot for collagenase II at a concentration of 0.3 µg/ml. FIG. 10D shows a Lineweaver-Burke plot for collagenase II at a concentration of 0.3 µg/ml. FIG. 10E shows a dose response curve of collagenase I (lower line) and collagenase II (upper line) activity using 50 µM of the protease substrate 5FAMcollagenPPT. Increasing concentrations of collagenase I and collagenase II were used (see x axis (µg/ml)). FIG. 10F shows a Michaelis-Menten plot for thermolysin at a concentration of 17 µg/ml. FIG. 10G shows a Lineweaver-Burke plot for thermolysin at a concentration of 17 µg/ml. FIG. 10H shows a dose response curve of thermolysin activity using 50 µM of the substrate 5FAMcollagenPPT. Increasing concentrations of thermolysin were used (see x axis (µg/ml)). $R^2$=0.99.

FIG. 15 shows the amino acid sequences of SEQ ID NO: 1 and SEQ ID NO: 2. SEQ ID NO: 1 represents the amino acid sequence of the minimal sequence of the protease substrate described herein. SEQ ID NO: 2 represents the amino acid sequence of the 5FAMcollagenPPT protease substrate.

FIG. 16 shows the polynucleotide sequence of SEQ ID NO: 3. SEQ ID NO: 3 represents the polynucleotide sequence of the thioredoxin-collagenPPT-SuperRenillaLuciferase bioluminescent protease substrate.

FIG. 17 shows the amino acid sequence of SEQ ID NO: 4. SEQ ID NO: 4 represents the amino acid sequence of the thioredoxin-collagenPPT-SuperRenillaLuciferase bioluminescent protease substrate. The repeating protease cleavage sequence is shown in bold and underlined.

DETAILED DESCRIPTION

Figure 1:
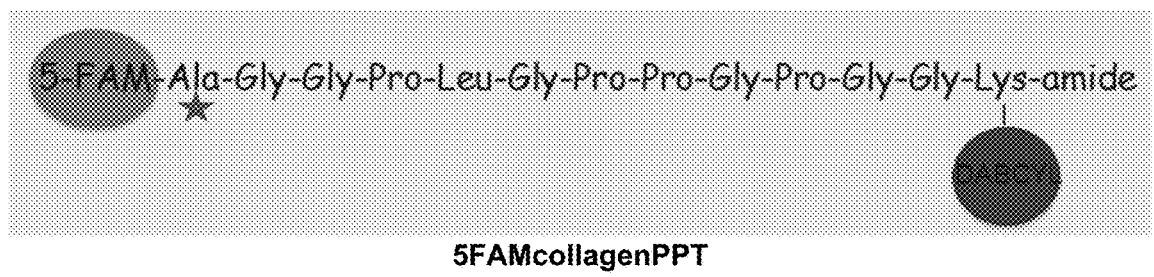
FIG. 1 shows the three letter amino acid sequence of the novel 5FAMcollagenPPT protease substrate. 5-carboxyfluorescein (5-FAM) (light grey circle) was conjugated to the peptide's N-terminus, while a 4-((4-(Dimethylamino)phenyl)azo)benzoic acid (DABCYL) (dark grey circle) was bound to the epsilon side chain of the terminal lysine.

The substrates, methods and kits disclosed herein are not limited to the particular configurations, process steps, and materials disclosed herein as such configurations, process steps, and materials may vary without materially varying from the scope and spirit. It is also to be understood that the terminology employed herein is used for the purpose of describing particular embodiments only and is not intended to be limiting. The examples are intended only to illustrate the disclosure in the application, and are not meant as limitations on it.

Clinical islet transplantation has proven to be an effective therapeutic method to treat type 1 diabetes mellitus and to improve glycemic control (Brennan 2015; Orr 2016; Qi 2014). Successful islet transplantation depends largely on the availability of suitable donor pancreata as well as the production of a sufficient amount of islets (Balamurugan 2014). It has been reported that there are one million islets in a normal healthy adult pancreas. Current isolation procedures fall short in isolating islets from a pancreas, which necessitates the use of multiple organs for isolating islets to reverse diabetes in a single recipient. This is due in part to the inability of enzymes to completely digest the pancreas to free the islets from the massive acinar tissue (Kaddis 2010), which results in inadequate islets isolated from a single pancreas. To overcome this challenge, a highly purified enzyme with low endotoxin levels was developed by Roche and Serva. Collagenase is the main component of the enzyme cocktail that is currently being used to digest the pancreas and to free the islets. Many centers use their own combination of digestive enzymes that is based on the experience of the islet isolation team (Qi 2015).

The essential procedure for isolating islets is to digest pancreatic tissue and free the islets from abundant extracellular matrix (ECM) (Johnson 1996). It has been reported that human pancreas contains the following ECM: collagen types I, III, IV, laminin, and fibronectin (Johnson 1996; Uscanga 1984; Kennedy 1987). An adult pancreas has an abundance of collagen bands and thus isolating islets has been a difficult and challenging task for obtaining sufficient islet yields. For successful digestion of the extracellular matrix, thermolysin/neutral protease is also added to the collagenase mixture. Optimal enzyme potency during pancreas digestion is necessary to synergistically degrade various collagen bands. Recently, a study conducted on 400 human pancreata showed that an appropriate ratio of class I and II collagenase is critical to collectively enhance the activity and potency of enzymatic digestion for maximum islet yields. The data clearly indicate that rapid digestion of the organ is essential to protect the quality of the isolated islets (Nano 2005). Recombinant collagenase I and II have been used for pancreas digestion for islet isolation, albeit the appropriate concentration/ratio has yet to be determined (Qi 2015; Brandhorst 2003; Balamurugan 2015).

Successful revascularization of islets occurs when the membrane and blood vessels surrounding the cells are well protected. Highly purified Liberase and mechanical agitation to dissociate islets from pancreatic tissue has advanced the method of isolating a high islet yield while maintaining cell integrity. However, there is still substantial variability among enzyme lots even among those proven to be most effective, and the stability of the enzyme continues to be a concern (Linetsky 1997). It is conceivable that the presence of neutral protease within collagenase may result in the degradation of the enzyme, thus affecting the activity, which may ultimately lead to inconsistency of reproducible results (Kin 2010).

Collagenase has been used for many years as the main enzyme to digest the pancreas from both animals and humans (Balamurugan 2014; Qi 2015; Fetterhoff 1995; Linetsky 1995; Bucher 2004; Cabellero-Corbalan 2009; Szot 2009). However, despite the effort to standardize the enzymatic procedure and manufacture a reliable GMP grade enzyme for pancreatic islet isolation (Szot 2009), there is still lot-to-lot variability (Yamamoto 2007). Currently, there are several methods available to measure collagenase (McCarthy 2008; Wunsch 1963). In particular, the Wunsch assay has been used to measure class II collagenase (Wunsch 1963), but was found to be unsuitable for measuring class I collagenase activity. It has been reported that *Clostridium histolyticum* produces 60% class I collagenase and 40% class II collagenase and neutral proteases (McCarthy 2008; Matsushita 1999). Hence, a more accurate and reliable method is needed to quantify enzyme activity.

Collagenase, thermolysin, and neutral protease are bacterial byproducts and very important enzymes for digesting pancreatic tissue (Qi 2015; Wu 2010; Van Wart 1985). Such enzymes are necessary in order to successfully isolate islets from the pancreas without compromising their quality. Current methods to mix an appropriate collagenase and thermolysin/neutral protease activity for pancreatic digestion were previously determined using random methodology (Brandhorst 2008; Kin 2008). Therefore having an accurate, highly sensitive, rapid, and reliable method to assess these enzymes is needed.

Novel protease substrates, comprising, consisting of, or consisting essentially of the amino acid sequence Ala-Gly-Gly-Pro-Leu-Gly-Pro-Pro-Gly-Pro-Gly-Gly (i.e., SEQ ID NO: 1, see FIG. 15) are provided herein. In certain embodiments, the protease substrates described herein can be used to assess the proteolytic activity of multiple products using a Fluorescence Resonance Energy Transfer (FRET) based assay. As shown herein, the novel 5FAMcollagenPPT protease substrate (i.e., SEQ ID NO: 2, see FIG. 1) is collagenase-specific and was not degraded by exocrine pancreatic proteases such as trypsin, chymotrypsin and elastase. The methods using the protease substrates described herein are simple and sensitive, and can be applied to measure enzyme activities of products from various vendors and sources. Furthermore, these methods can be used to monitor proteolytic activity and to examine the effects that any additional activator or inhibitor may have on enzymatic function, particularly during the tissue digestion process.

The methods described herein are extremely sensitive for detecting enzyme proteolytic activity and can determine the kinetic parameters of various enzymes using micromolar concentrations of substrate (Tokima-Roszyk 2014; Saikumari 2008; Salamone 2010; Baici 1980). The novel protease substrate 5FAMcollagenPPT contains a 5-CarboxyFluorescein-Aminohexyl Amidite (5-Fam) fluorogenic group. The principle of the FRET assay is based on the fact the fluorophore donor and the fluorophore acceptor (quencher) are in sufficient proximity in the substrate to allow a resonance energy transfer between the fluorophore and the quencher. The change in resonance energy transfer and increase in fluorescence intensity upon substrate cleavage therefore provides a convenient way to monitor the enzymatic reaction.

A precise and sensitive assay to evaluate and quantify the activity of collagenase and other bacterial proteases is a critical component in obtaining high quality islets, and would allow islets to be isolated without compromising their integrity or quantity. Collagenase, thermolysin, and neutral protease need to be applied diligently for the optimal liberation of intact islets or stem cells from pancreas tissue. Therefore, it is paramount to meticulously quantify the specific activity of these bacterially produced enzymes before use. Thus, the substrates, methods, and kits provided herein may be used to evaluate the activity of certain bacterial proteases used for preparation of islets for islet transplantation and research applications. Additionally, the substrates, methods, and kits provided herein may also be used to measure and evaluate the activity of certain bacterial proteases used in various other types of tissue dissociation, cell isolation, and/or cell detachment applications to maximize the yield of functionally viable dissociated tissue or cells. Further, the substrates, methods, and kits provided herein may also be used to measure and evaluate the activity of certain bacterial proteases that are available in certain drugs used to treat diseases, such as those diseases that involve an excess of inelastic collagen. For example, the substrates, methods, and kits may also be used to measure and evaluate the activity of certain bacterial proteases that cause disease, such as botulinum neurotoxins (BoNTs). Since BoNTs are also important medical and cosmetic agents, used to treat dystonias, blepharospasms, hyperhidrosis, and other neurological diseases, the substrates, methods, and kits disclosed herein may also be used to measure and evaluate the activity in medical and cosmetic agents containing BoNTs.

Provided herein are robust and highly sensitive assays to detect the presence and activity of certain prokaryotic proteases using novel, synthetic protease substrates. In certain embodiments, the prokaryotic protease may be a bacterial protease. In certain embodiments the protease substrate may be a fluorogenic or bioluminescent substrate. The rationale for the development of these substrates was to accurately measure enzymatic activities with the required sensitivity in order to optimize the formulation of a cocktail of enzymes used for pancreatic digestion in the preparation of islets at maximum yield. In certain embodiments, the cocktail of enzymes includes a mixture of collagenase and one or more bacterial proteases. In certain embodiments, the one or more bacterial proteases may be thermolysin, neutral protease, and dispase. The protease substrates described herein are highly sensitive and can be used for measuring the activities of one or more bacterial proteases used in tissue or cell preparation such as collagenase, thermolysin, neutral protease, and dispase. In certain embodiments, the turnaround time for the assay is expeditious, and can be completed within about one hour.

Protease Substrates:

According to certain embodiments, the protease substrate described herein may comprise, consist of, or consist essentially of the amino acid sequence:

Ala-Gly-Gly-Pro-Leu-Gly-Pro-Pro-Gly-Pro-Gly-Gly (i.e., SEQ ID NO: 1, see FIG. 15). In certain embodiments, the protease substrate may comprise, consist of, or consist essentially one or more amino acid sequences of SEQ ID NO: 1. For example, in certain embodiments, the protease substrate may comprise, consist of, or consist essentially of repeating sequences of SEQ ID NO: 1. In certain embodiments, the protease substrate may comprise two, three, four, five, six, seven, eight, nine, or ten amino acid sequences of SEQ ID NO: 1. In certain embodiments, the protease substrate comprising two or more amino acid sequences of SEQ ID NO: 1 does not have any amino acids separating the repeating amino acid sequences of SEQ ID NO: 1. In certain embodiments, the protease substrate comprising repeating amino acid sequences of SEQ ID NO: 1 may have one or more amino acids separating the repeating amino acid sequences of SEQ ID NO: 1.

In certain embodiments, the protease substrate may comprise, consist of, or consist essentially of the amino acid sequence:

5-FAM-Ala-Gly-Gly-Pro-Leu-Gly-Pro-Pro-Gly-Pro-Gly-Gly-Lys[DABCYL]-amide (i.e., SEQ ID NO: 2; see FIG. 1, FIG. 15, and Table 1).

TABLE 1

The sequence of 5FAMcollagenPPT (i.e., SEQ ID NO: 2).

| Amino Acid Position Number | 1 Letter Code | 3 Letter Code | Amino acid name and modification |
|---|---|---|---|
| 1 | [5-Fam]A | [5-Fam]Ala | Alanine with a 5-carboxyfluorescein conjugated (as illustrated by SEQ ID NO: 2) |
| 2 | G | Gly | Glycine |
| 3 | G | Gly | Glycine |
| 4 | P | Pro | Proline |
| 5 | L | Leu | Leucine |
| 6 | G | Gly | Glycine |
| 7 | P | Pro | Proline |
| 8 | P | Pro | Proline |
| 9 | G | Gly | Glycine |
| 10 | P | Pro | Proline |
| 11 | G | Gly | Glycine |
| 12 | G | Gly | Glycine |
| 13 | K[DABCYL] | Lys[DABCYL] | Lysine with DABCYL conjugated to its ε-amino group |

Figure 2:
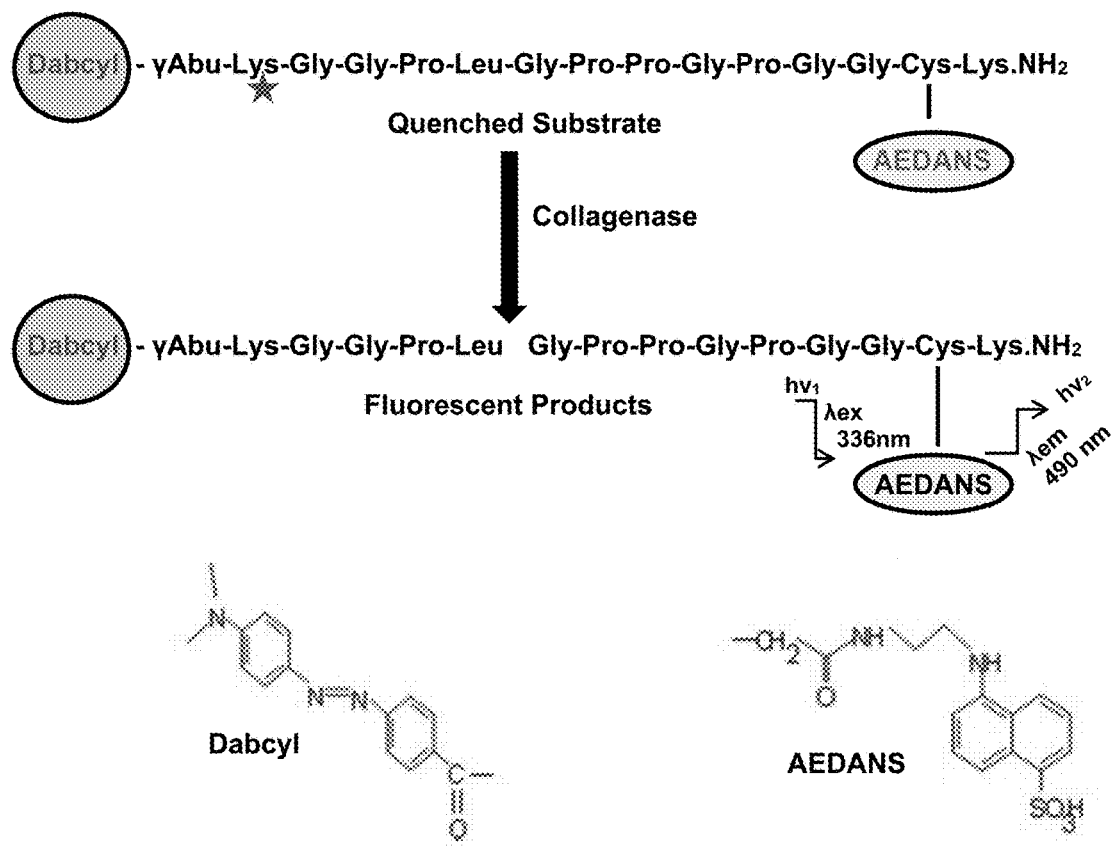
FIG. 2 shows the sequence of a previously published peptide, "Peptide 1" (see FIG. 1 of Saikumari, 2008), that can be cleaved by collagenase. Peptide 1 differs from the protease substrate 5FAMcollagenPPT in both structure and function. For example, Peptide 1 and 5FAMcollagenPPT differ in amino acid length and sequence, type of fluorophore attached, and position of attachment for both the fluorophore and quencher. Peptide 1 contains an N-terminus DABCYL quencher (dark grey circle) and a C-terminus 5-[2-(acetamido) ethylamino] naphthalene-1-sulfonic acid (AE-DANS) (light grey oval) fluorophore. Peptide 1 is resistant to attack by thermolysin (Saikumari, 2008, see Abstract), unlike the protease substrate 5FAMcollagenPPT, which was cleaved by thermolysin (see FIGS. 3E, 3F, 4E and 4F). Additionally, compared with Peptide 1, the protease substrate 5FAMcollagenPPT demonstrated significantly better kinetic parameters (see $V_{max}$ values for 5FAMcollagenPPT in FIGS. 3, 4 and 10).

The protease substrate 5FAMcollagenPPT described herein unexpectedly differs from previously published peptides (e.g., Saikumari, 2008, see "Peptide 1" and FIG. 2 and Van Wart, 1985) in both structure and function. For example, the protease substrate 5FAMcollagenPPT differs from Peptide 1 in amino acid length and sequence. 5FAMcollagenPPT is thirteen amino acids long, whereas Peptide 1 is fifteen amino acids long; the differences in amino acids are found at the N- and C-terminal regions of the peptides. Additionally, specific amino acid changes in 5FAMcollagenPPT rendered the peptide resistant to trypsin, but cleavable by thermolysin (e.g., the alanine at position 1 in the 5FAMcollagenPPT is a lysine at the corresponding position 2 in Peptide 1) (compare FIG. 1 with FIG. 2). Note that although Saikumari et al. report that Peptide 1 is resistant to trypsin (see abstract and FIG. 3 of Saikumari, 2008), recent experiments performed with Peptide 1 and trypsin showed that trypsin was able to cleave Peptide 1 (data not provided herein), which differs from the results reported by Saikumari et al. Significantly, Peptide 1 contains a lysine at position 2, whereas 5FAMcollagenPPT has an alanine at position 1, which corresponds to position 2 of Peptide 1 (see FIGS. 1 and 2, and Table 1, stars indicate corresponding residues). This difference rendered Peptide 1 cleavable by trypsin at the C-terminus of the lysine at position 2 (data not provided herein). Based on these findings, it is unclear how and why Peptide 1 was reported to be resistant to trypsin as described in Saikumari, 2008. Additionally, Peptide 1 was reported to be resistant to thermolysin (see abstract and FIG. 3 of Saikumari, 2008), but experiments with 5FAMcollagenPPT and thermolysin indicated that thermolysin cleaves 5FAMcollagenPPT at four different cleavage sites (see Table 4 and Table 8 below). Therefore, 5FAMcollagenPPT and Peptide 1 differ not only in the structure of their amino acid sequences, but also in their ability to be cleaved by different proteases.

Further, the type of fluorophore moiety attached to each peptide and the location of attachment of the fluorophore and quencher is different between the two peptides. For example, 5FAMcollagenPPT has a 5-FAM conjugated to the N-terminus alanine; whereas, Peptide 1 has an AEDANS fluorophore conjugated to a cysteine near the C-terminus of the peptide (compare FIG. 1 with FIG. 2). As AEDANS is an inefficient fluorophore, 5FAMcollagenPPT was designed to include a 5-FAM fluorophore which is a much more efficient fluorophore in terms of quantum yield. Also, the DABCYL on Peptide 1 is located on the N terminus, whereas the DABCYL is positioned on the lysine side chain epsilon amino group of 5FAMcollagenPPT. The positioning of the DABCYL on the lysine of 5FAMcollagenPPT is much more stable than having an alkylated cysteine residue, such as the Cys[AEDANS] of Peptide 1.

As shown in the examples below, these structural changes between Peptide 1 and 5FAMcollagenPPT resulted in the unexpected superior sensitivity and specificity of 5FAMcollagenPPT for a variety of bacterial proteases as shown by the Michaelis Constant ($K_m$-) and maximum velocity ($V_{max}$) values provided in Tables 5 and 6, and FIG. 5. The $K_m$ and $V_{max}$ were determined using the Michaelis-Menten and Lineweaver-Burk plots shown in at least FIGS. 3A-H, 4A-H and 10A-H. $V_{max}$ represents the maximum velocity or rate achieved by the system, which occurs when all enzyme active sites are saturated with substrate. As such, $V_{max}$ reflects how fast the enzyme can catalyze the reaction. An enzyme's $K_m$ describes the substrate concentration at which half the enzyme's active sites are occupied by substrate, which is half of $V_{max}$. Thus, a high $K_m$ means that a lot of substrate must be present to saturate the enzyme, indicating that the enzyme has low affinity for the substrate. However a low $K_m$ means that only a small amount of substrate is needed to saturate the enzyme, indicating a high affinity for substrate.

The protease substrate 5FAMcollagenPPT described herein has the unique characteristic of being cleaved by bacterial (prokaryotic) proteases such as class I and class II collagenase (collagenase I and collagenase II, respectively), class I/II collagenase (collagenase I//II) thermolysin, neutral protease, and dispase (Table 2).

TABLE 2

Enzymes that can cleave 5FAMcollagenPPT and/or prior art Peptide 1.

| 5FAMcollagenPPT | Peptide 1 |
| --- | --- |
| collagenase | collagenase |
| thermolysin | trypsin* |
| neutral protease | |
| dispase | |
| Botulinum neurotoxin A and B | unknown |

*Note that this result is disputed (see above).

This is in contrast to the previously published Peptide 1, which is cleaved exclusively by collagenase and is resistant to cleavage by thermolysin (Saikumari, 2008) (see Table 2 and Table 3) (note that although Saikumari et al reports no cleavage of Peptide 1 by trypsin, Peptide 1 was recently shown to be cleaved by trypsin (data not provided herein)).

TABLE 3

Enzymes that do not cleave 5FAMcollagenPPT and/or prior art Peptide 1.

| 5FAM collagenPPT | Peptide 1 |
| --- | --- |
| trypsin | trypsin* |
| chymotrypsin | thermolysin |
| elastase | |

*Note that this result is disputed (see above).

Moreover, the protease substrate 5FAMcollagenPPT is resistant to cleavage by mammalian pancreatic proteases such as trypsin, chymotrypsin and elastase (Table 3). As such, the novel protease substrate 5FAMcollagenPPT is useful for tissue dissociation and cell isolation, such as islet cell, primary cell, or stem cell preparation.

As shown in the examples below, cleavage of the protease substrate 5FAMcollagenPPT by certain proteases (i.e., collagenase I and neutral protease) was enhanced significantly in the presence of $CaCl_2$. Cleavage of the protease substrate by all bacterial proteases tested was significantly decreased in the presence of zinc and the chelating agent EGTA. The pH of the buffer also influence enzymatic activity as results showed that the optimal pH range is 6.8-7.5.

In certain embodiments, the protease substrate described herein may comprise at least one protease cleavage site. In certain embodiments, the protease cleavage site may be a bacterial protease cleavage site. In certain embodiments, the protease substrate described herein may comprise at least one protease cleavage site as indicated in Table 4 and FIG. 14. For example, the protease substrate may comprise one or more collagenase I cleavage sites, one or more collagenase II cleavage sites, one or more thermolysin cleavage sites, one or more neutral protease cleavage sites, and/or one or more dispase cleavage sites.

TABLE 4

Specific protease cleavage sites of 5FAMcollagenPPT
5FAMcollagenPPT
5Fam-Ala1-Gly2-Gly3-Pro4-Leu5-Gly6-Pro7-Pro8-Gly9-Pro10-Gly11-Gly12-Lys13[Dabcyl]

| Cleavage Site | Protease* |
| --- | --- |
| Gly3-Pro4 | Col. NB1 |
| Pro4-Leu5 | Therm., NP NB, Col. NB1 |
| Leu5-Gly6 | Col. I, Col. II, Them., NP NB, Col. I/II |
| Pro8-Gly9 | Col. I, Col. II, Them., NP NB, Col. NB1, Col. I/II |
| Gly11-Gly12 | Therm. |

*Col. I = Collagenase I; Col. II = Collagenase II; Therm. = Thermolysin; NP NB = Neutral Protease NB; Col. NB1 = Collagenase NB1; Col. I/II = Collagenase I/II Table data based on results from Table 8.

In certain embodiments, the protease substrate may comprise one or more collagenase I cleavage sites. For example, in certain embodiments, the protease substrate may comprise one or more collagenase I cleavage sites selected from a Leu5-Gly6 cleavage site, a Pro8-Gly9 cleavage site, and/or any combination thereof (see Table 4, Table 8, FIG. 14, and SEQ ID NOs: 1 and 2).

In certain embodiments, the protease substrate may comprise one or more collagenase II cleavage sites. For example, in certain embodiments, the protease substrate may comprise one or more collagenase II cleavage sites selected from a Leu5-Gly6 cleavage site, a Pro8-Gly9 cleavage site, and/or any combination thereof (see Table 4, Table 8, FIG. 14, and SEQ ID NOs: 1 and 2).

In certain embodiments, the protease substrate may comprise one or more thermolysin cleavage sites. For example, in certain embodiments, the protease substrate may comprise one or more thermolysin cleavage sites selected from a Pro4-Leu5 cleavage site, a Leu5-Gly6 cleavage site, a Pro8-Gly9 cleavage site, a Gly11-Gly12 cleavage site, and/or any combination thereof (see Table 4, Table 8, FIG. 14, and SEQ ID NOs: 1 and 2).

In certain embodiments, the protease substrate may comprise one or more neutral protease NB cleavage sites. For example, in certain embodiments, the protease substrate may comprise one or more neutral protease NB cleavage sites selected from a Pro4-Leu5 cleavage site, a Leu5-Gly6 cleavage site, a Pro8-Gly9 cleavage site, and/or any combination thereof (see Table 4, Table 8, FIG. 14, and SEQ ID NOs: 1 and 2).

In certain embodiments, the protease substrate may comprise one or more collagenase NB1 cleavage sites. For example, in certain embodiments, the protease substrate may comprise one or more collagenase NB1 cleavage sites selected from a Gly3-Pro4 cleavage site, a Pro4-Leu5 cleavage site, a Pro8-Gly9 cleavage site, and/or any combination thereof (see Table 4, Table 8, FIG. 14, and SEQ ID NOs: 1 and 2).

In certain embodiments, the protease substrate may comprise one or more collagenase I/I cleavage sites. For example, in certain embodiments, the protease substrate may comprise one or more collagenase I/I cleavage sites selected from a Leu5-Gly6 cleavage site, a Pro8-Gly9 cleavage site, and/or any combination thereof (see Table 4, Table 8, FIG. 14, and SEQ ID NOs: 1 and 2).

In certain embodiments, the protease substrate may comprise one or more protease cleavage sites selected from collagenase I, collagenase II, thermolysin, collagenase NB1, collagenase I/I, neutral protease NB cleavage sites, and/or any combination thereof.

In certain embodiments, the protease may be produced from native/natural microorganisms. In certain embodiments, the protease may be recombinant enzyme(s) produced by genetic engineering.

Fluorogenic protease substrates: In certain embodiments, the protease substrate described herein may be a fluorogenic protease substrate. In certain embodiments, the fluorogenic protease substrate may comprise one or more amino acid sequences of SEQ ID NO: 1. In certain embodiments, the one or more amino acid sequences may comprise at least one bacterial protease cleavage site as described above and shown in Tables 4 and 8. In certain embodiments, the fluorogenic protease substrate may be resistant to cleavage by trypsin, chymotrypsin and elastase. In certain embodiments, the fluorogenic protease substrate may comprise, consist of or consist essentially of SEQ ID NO: 2 (i.e., 5FAMcollagenPPT).

In certain embodiments, the fluorogenic protease substrate may comprise a donor fluorophore and an acceptor having an absorbance spectrum overlapping the emission spectrum of the donor fluorophore. In certain embodiments, the donor fluorophore may comprise one or more fluorophores. For example, the donor fluorophore may comprise one or more fluorophores including 5-carboxyfluorescein (5-FAM), 4-methylumbelliferone (4-MU), and/or any other fluorophore known to one of ordinary skill in the art. In certain embodiments, the donor fluorophore may be conjugated at or near the N terminus of the protease substrate. In certain embodiments, the donor fluorophore may be conjugated to the protease substrate via a peptide bond at or near the N-terminus, which enhances the stability of the protease substrate. In some embodiments, the donor fluorophore may be conjugated to the alpha-amino group of an amino acid residue. In other embodiments, the donor fluorophore may be conjugated to the epsilon-amino group of an amino acid residue. In certain embodiments, the amino acid residue may be alanine.

In certain embodiments provided herein, the acceptor may be a dark quencher. For example, the acceptor may be 4-((4-(dimethylamino)phenyl)azo)benzoic acid (i.e., DABCYL). In some embodiments, the DABCYL may be conjugated at or near the C-terminus of the fluorogenic protease substrate. In some embodiments, the DABCYL may be conjugated to the epsilon amino group of an amino acid residue at or near the C-terminus of the fluorogenic protease substrate. In certain embodiments, the amino acid residue at or near the C-terminus of the protease substrate may be a lysine. Upon excitation, the DABCYL suppresses the fluorescence emission of the fluorogenic protease substrate when the protease substrate is not cleaved and the donor fluorophore and DABCYL remain close together. However, when the protease substrate is cleaved by the protease, the donor fluorophore and DABCYL are separated and the donor fluorophore emits light energy upon excitation. In certain embodiments, the fluorogenic protease substrate may be capable of eliciting a detectable fluorescence signal when modified by a protease.

Bioluminescent Protease Substrates:

In certain embodiments, the protease substrate described herein may be a bioluminescent protease substrate. In certain embodiments, the bioluminescent protease substrate may be capable of eliciting a detectable luminogenic signal when modified by a protease. In certain embodiments, the bioluminescent protease substrate may comprise one or more luciferase proteins and/or fragments thereof. In certain embodiments, the bioluminescent protease substrate may comprise one or more novel engineered variants of recombinant luciferase proteins. For example, the bioluminescent protease substrate may comprise an amino acid sequence of the Super *Renilla*-Luciferase protein and/or a fragment thereof. Luminescent luciferase proteins have the ability to emit light at multiple wavelengths. The bioluminescent protease substrates provided herein have the advantage that they can be produced inexpensively and in large quantities from cultures of engineered *Escherichia coli* bacteria. In certain embodiments, the bioluminescent protease substrates may be produced in yeast or insect cells. Furthermore, bioluminescent protease substrates reduce the requirements for expensive instrumentation. Simple and very sensitive and even portable luminometers can be used to detect the presence of proteases instead of much more expensive fluorometric instrumentation. Additionally, luminescent based assays can reduce or omit the requirement for a light source and provide greater signal-to-noise ratios. Bioluminescent light in particular, can be detected using less complex means such as with miniaturized photomultipliers or microscopic avalanche photodiodes. Furthermore, potential interference from background fluorescence due to inert components of a microfluidic device is alleviated.

Figure 18:
FIG. 18 shows the polynucleotide and amino acid sequence of the thioredoxin-collagenPPT-SuperRenillaLuciferase bioluminescent protease substrate. Note that the thioredoxin-collagenPPT-SuperRenillaLuciferase substrate is comprised of a fusion protein containing a thioredoxin tag (trx tag), a serine-glycine linker, a polyhistidine tag (His tag), a serine-glycine linker, a thrombin cleavage site sequence (thrombin), an S tag (S tag), an enterokinase cleavage site sequence (enterokinase), two repeating protease substrate sequences (Protease Substrate Sequence ×2), and a Super *Renilla*-Luciferase sequence (SRLuc) followed by a polyhistidine tag (His tag).
Figure 18:
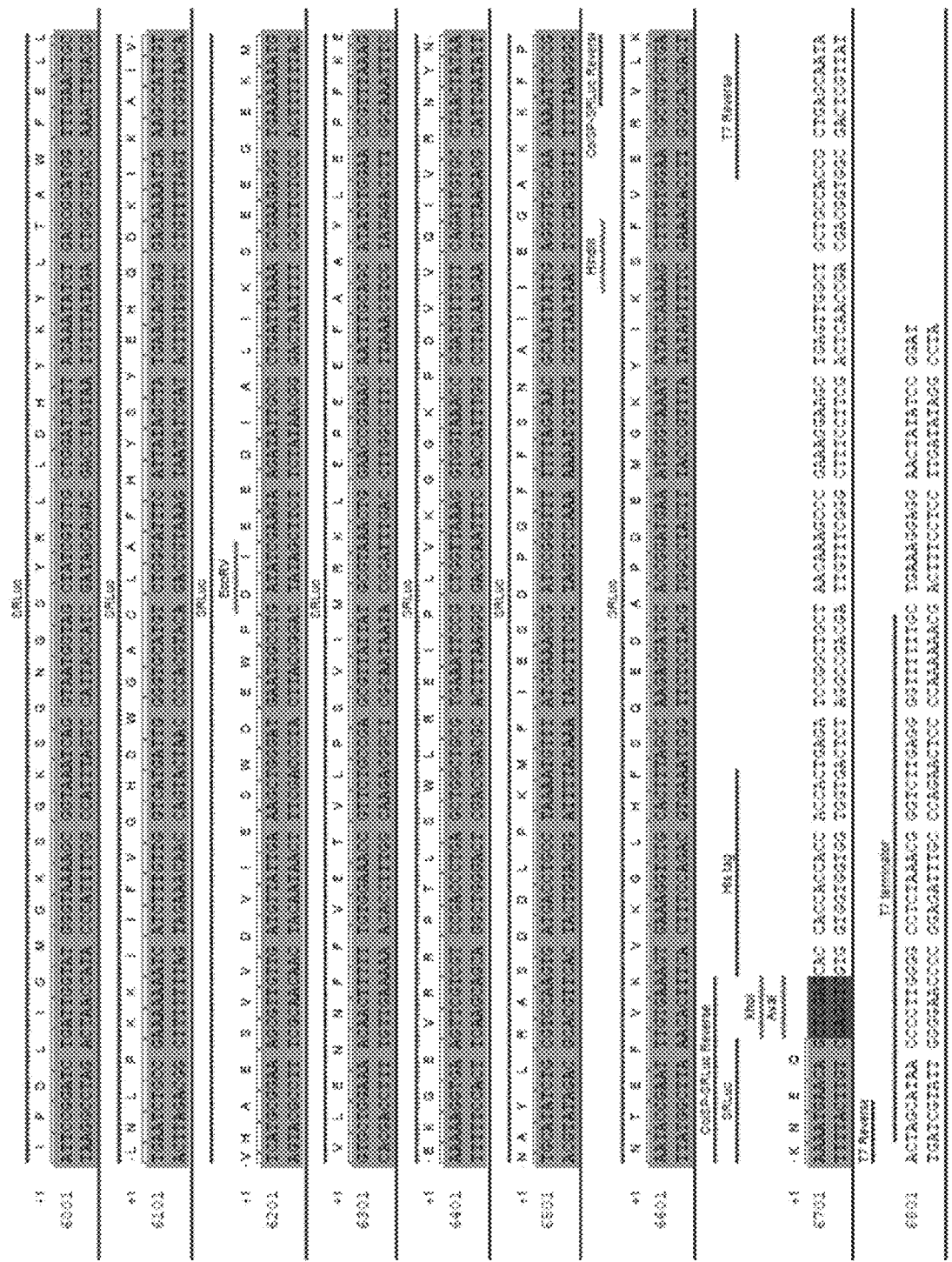

In certain embodiments, a bioluminescent protease substrate may comprise, consist of, or consist essentially of one or more amino acid sequences of SEQ ID NO: 1. In certain embodiments, the one or more amino acid sequences of SEQ ID NO: 1 may comprise at least one bacterial protease cleavage site as described above and shown in Tables 4 and 8, and FIG. 14. In certain embodiments, the bioluminescent protease substrate may comprise, consist of, or consist essentially of the amino acid sequence of SEQ ID NO: 4 (see FIG. 17 for the amino acid sequence of thioredoxin-collagenPPT-SuperRenillaLuciferase; see SEQ ID NO: 3 and FIG. 16 for the polynucleotide sequence of thioredoxin-collagenPPT-SuperRenillaLuciferase). FIG. 18 shows the double stranded DNA sequence and the amino acid sequence of the thioredoxin-collagenPPT-SuperRenillaLuciferase bioluminescent protease substrate cloned into a pET-32b(+) vector. As shown in FIG. 18, the thioredoxin-collagenPPT-SuperRenillaLuciferase substrate comprises a fusion protein containing a thioredoxin tag, a serine-glycine linker, a polyhistidine tag, a serine-glycine linker, a thrombin cleavage site sequence, an S tag, an enterokinase cleavage site sequence, two repeating protease substrate sequences (i.e., two repeating amino acid sequences of SEQ ID NO: 1), and a Super *Renilla*-Luciferase sequence followed by a polyhistidine tag. In certain embodiments, the bioluminescent protease substrate may comprise one or more sequences selected from a positive control cleavage site sequence, an affinity tag sequence, and a linker sequence. Examples of positive control cleavage site sequences include, without limitation, a thrombin cleavage site sequence and an amino acid sequence recognized by the Tobacco Etch Virus protease (i.e., the sequence "ENLYFQG"). Examples of affinity tag sequences include, without limitation, polyhistidine tags, glutathione-S-transferase (GST) tags, maltose binding protein (MBP) tags, thioredoxin (TRX), and/or any affinity tag sequence known to one of ordinary skill in the art. Examples of linker sequences include, without limitation, one or more serine and/or glycine amino acid residues. In certain embodiments, the bioluminescent protease substrate may comprise serine, glycine, and/or serine-glycine linkers to optimize the turnover rate for protease cleavage of the substrates. In certain embodiments, the bioluminescent protease substrate may be resistant to cleavage by trypsin, chymotrypsin and elastase.

Methods for Detecting Proteases:

Methods for detecting the presence of one or more proteases in a sample are provided. These methods may be used for detecting and quantifying the activity of the one or more proteases, such as the specific activity of the enzyme. In certain embodiments, the protease may be a bacterial protease. In certain embodiments, the methods for detecting the presence of one or more bacterial proteases in a sample comprise exposing the sample putatively containing the one or more bacterial proteases to an enrichment matrix comprising one or more bacterial protease substrates that are capable of eliciting a detectable signal when modified by the one or more bacterial proteases. In certain embodiments, the methods for detecting the presence of one or more bacterial proteases in a sample may further comprise measuring the level of change in detectable signal and detecting the presence of the one or more bacterial proteases when the level of changes in the detectable signal in the sample is elevated.

In certain embodiments, the one or more bacterial protease substrates may be a fluorogenic protease substrate and/or a bioluminescent protease substrate as described herein. In certain embodiments, the one or more bacterial proteases comprise class I collagenase, class II collagenase, thermolysin, neutral protease, and dispase proteases.

In certain embodiments, if the bacterial protease substrate is a fluorogenic protease substrate (i.e., 5FAMcollagenPPT), the bacterial protease substrate may be capable of eliciting a detectable fluorescence signal when modified by the protease. In some embodiments, the methods for detecting the presence of the protease also include measuring a change in the detectable fluorescence signal in the sample. Upon protease substrate cleavage, the detectable signal may be measured. In some embodiments, the signal may be detected after elution of the sample containing the detectable signal. Fluorescence may be detected using a handheld ultraviolet (UV) light, a fluorescence excitation and/or detecting tool, device or any suitable commercially available fluorometer. In some embodiments, a Victor X2 multilabel plate reader (Perkin Elmer, Shelton, Conn.) may be used to detect fluorescence.

The methods described herein may also include a step of detecting the presence of the protease when the level of the change in the detectable fluorescence signal is elevated. In some embodiments, the level of the change in the detectable fluorescence signal is calculated as a change in relative fluorescence unit (RFU). In one embodiment, the level of the change in the fluorescence signal may be elevated when the level of the change in the signal is greater than or equal to a predetermined level of background fluorescence. In some embodiments, the predetermined level of background fluorescence may be the fluorescent level of a protease-free control sample. In some embodiments, the level of the change in the detectable fluorescence signal is elevated when the level is significantly greater than the level of change in detectable fluorescence signal from a negative control sample. As described herein, a "negative control" sample comprises a sample that does not comprise a protease, such as a protease-free sample.

In certain embodiments, if the bacterial protease substrate is a bioluminescent protease substrate, the bacterial protease substrate may be capable of eliciting a detectable luminogenic signal when modified by the protease. In some embodiments, the method for detecting the presence of the protease also includes measuring a change in the detectable luminogenic signal in the sample. Upon protease substrate cleavage, the detectable signal may be measured. In some embodiments, the signal may be detected after elution of the sample containing the detectable signal.

In certain embodiments, the enrichment matrix may comprise immunoaffinity or affinity beads that may be used for immobilization of the protease and/or protease substrate. For example, the beads may be cyanogen-bromide (CNBr) activated Sepharose beads, protein-A, protein-G, or protein A/G conjugated Sepharose, agarose, magnetic, nickel nitrilotriacetic (Ni-NTA), or glutathione beads. In certain embodiments, the protease and/or protease substrate may be immobilized onto the beads through any method known to a person having ordinary skill in the art. For example, in certain embodiments, the enrichment matrix may comprise Ni-NTA beads that immobilize the protease substrate to the beads through binding of a polyhistidine tag of the protease substrate to the Ni-NTA beads.

Additionally, in some embodiments, the beads may be coupled and cross-linked to one or more protease substrate specific antibodies that bind a protease substrate. In certain embodiments, if the protease substrate is a fluorogenic protease substrate, the protease substrate specific antibodies may bind a region of the fluorogenic protease substrate including the donor fluorophore, the acceptor, or one or more amino acids of the protease substrate amino acid sequence. For example, the enrichment matrix may comprise protein-A/G conjugated agarose beads coupled and cross linked to anti-FITC antibodies that bind the fluorescent 5-FAM label conjugated to the protease substrate. In another example, the enrichment matrix may comprise protein-A/G conjugated agarose beads coupled and cross liked to anti-DABYCL antibodies that bind the DABYCL conjugated to the protease substrate. In yet another example, the enrichment matrix may comprise protein-A/G conjugated agarose beads coupled and cross linked to sequence-specific antibodies that one or more amino acids of the protease substrate amino acid sequence.

In certain embodiments, if the protease substrate is a bioluminescent protease substrate, the protease substrate specific antibodies may bind a region of the bioluminescent protease substrate. In certain embodiments, the protease substrate specific antibodies may bind one or more amino acids of the protease substrate amino acid sequence.

In some embodiments, the beads may be coupled and cross-linked to one or more protease specific antibodies that bind a protease. In certain embodiments, the enrichment matrix comprises a double-affinity matrix that includes beads that bind both protease specific antibodies and protease substrate specific antibodies.

In certain embodiments, exposure of the sample to an enrichment matrix occurs under conditions permitting binding of the protease to the antibody and a modification of the protease substrate by the protease. In certain embodiments, this exposure may occur in the dark. In one embodiment, the sample is exposed to the enrichment matrix prior to being exposed to the protease substrate.

In certain embodiments, the enrichment matrix may be provided in an immunosorbent support comprised of loose beads or a fixed column. Any variety of one or more commercialized columns may be used including, but not limited to, gravity-flow columns, spin columns, and pressure columns. In some embodiments, two or more columns may be used. Additionally, affinity microcolumns may be used. In some embodiments, pipette tip columns containing affinity microcolumns mounted into pipette tips may be used. In some examples, the pipette tips may be disposable. For example, the affinity microcolumns may be dextran glass columns from Intrinsic Bioprobes, Inc. (acquired by Thermo Fischer Scientific) and may contain microcolumns mounted into pipette tips. The affinity microcolumns mounted into pipette tips may be used as described in U.S. Pat. No. 7,087,164 B2. In some examples, the microcolumns mounted into pipette tips may be used in conjunction with an inexpensive, robust automated high-throughput method for detecting protease in biological samples. For example, a microcolumn robotic pipetting workstation system may be used for the automated microcolumn based protease detection system for use as a high-throughput system. In other examples, the microcolumns mounted into pipette tips may be used in conjugation with an electronic multichannel pipettor.

The methods, substrates, and kits provided herein may be used to determine if there are any traces of bacterial protease activity post cell culture. In certain embodiments, post cell culture may be post islet cell culture, post stem cell culture, or post primary cell culture. In some embodiments, the methods, substrates, and kits provided herein may be used for monitoring bacterial protease activity and observing the effects that any enhancer or inhibitor may have on the bacterial protease enzymatic function. In certain embodiments, monitoring bacterial protease activity occurs during the pancreas digestion process. In some embodiments, the one or more bacterial proteases may be selected from the group consisting of collagenase I, collagenase II, thermolysin, neutral protease, and dispase as described herein.

According to some embodiments, the methods, substrates, and kits may also be used for identifying and monitoring the purity and quality of bacterial proteases. With this information, an appropriate ratio of lytic enzymes can be established for optimal islet yield even from suboptimal organ recoveries. In certain embodiments, the methods, substrates, and kits provided herein may be used to detect the presence of one or more bacterial proteases used in the preparation of islet cells. The methods, substrates, and kits described herein may also be used to identify other enzymes or products from other sources of bacteria, organisms, plants, yeast, insect or recombinant enzymes.

Due to its sensitivity in detecting enzyme activity of proteases involved in pancreas digestion, the 5FAMcollagenPPT protease substrate may replace the expensive procedures used to test enzyme activity for pancreas digestion. It would be immensely beneficial to evaluate multiple enzymes using this protease substrate so that appropriate enzyme cocktails may be prepared for tissue dissociation with minimal cell death.

Furthermore, the bacterial proteases such as collagenase, thermolysin and neutral protease, are not only relevant for pancreas digestion and enhanced isolation of islets, but they may also be useful for other tissue dissociation, cell isolation, or cell detachment protocols. For example, bacterial proteases may be used to isolate primary cells or stem cells. Thus, in some embodiments, the methods, substrates, and kits provided herein may also be useful for measuring and evaluating the activity of bacterial proteases that assist in the isolation of primary cells and stem cells.

In certain embodiments, the methods, substrates, and kits described herein may also be used for measuring the activity of collagenase (e.g., *clostridium histolyticum* collagenase) which is used in certain drugs to treat diseases that involve an excess of inelastic collagen. For example, in certain embodiments, the diseases that involve an excess of inelastic collagen may be Dupuytren's contracture (see, e.g., U.S. Pat. No. 5,589,171), Peyronie's disease, Frozen Shoulder, Cellulite reductions, and human and canine lipomas. In certain embodiments, the drug used to treat diseases that involve an excess of inelastic collagen may be XIAFLEX®. In certain embodiments the protease substrate may be used for measuring the activity of *clostridium histolyticum* in the drug.

In certain embodiments, the methods disclosed herein may be performed in a solution having a particular pH. As shown in Example 2, the cleavage activity of collagenase II, thermolysin, and neutral protease was influenced by pH. In certain embodiments, the methods provided herein may be performed in a solution having a pH within a range of 6.0 to 8.0. In certain embodiments, the methods may be performed in a solution having a pH within a range of 6.5. to 7.5. In certain embodiments, the methods may be performed in a solution having a pH within a range of 6.8. to 7.5. In certain embodiments, the methods provided herein may be used to detect protease activity in a digestion solution during islet isolation.

The cleavage activity of collagenase class I and II, thermolysin, and neutral protease was also influenced by the presence of $CaCl_2$, zinc, and chelating agents. As shown in Example 2, the enzyme activity of collagenase I and neutral protease was enhanced significantly in the presence of $CaCl_2$. Results also showed that enzymatic activity of all enzymes tested was significantly decreased in the presence of zinc and the chelating agent, ethylene glycol-bis(β-aminoethyl ether)-N,N,N',N'-tetraacetic acid (EGTA). In certain embodiments, the methods provided herein may be performed in the presence of $CaCl_2$. In certain embodiments, the methods provided herein are not performed in the presence of zinc (e.g., $ZnSO_4$ or $ZnCl_2$). In certain embodiments, the methods disclosed herein are not performed in the presence of a chelating agent, such as EGTA.

In certain embodiments, the methods provided herein may be used to enhance the success of islet cell preparation for islet transplantation. In certain embodiments, the islet cells are transplanted into patients suffering from type 1 diabetes mellitus (T1DM).

Kits for Protease Detection:

According to some embodiments provided herein, kits are described using the components of the assay as described herein. In certain embodiments, the kits may include an enrichment matrix and at least one or more protease substrates as described herein. For example, the kit may comprise one or more fluorogenic protease substrates and/or one or more bioluminescent protease substrates as described herein. In certain embodiments, the enrichment matrix may comprise at least one or more immunoaffinity beads as described herein. For example, the beads may be coupled and cross-linked to a protease-specific antibody and/or protease substrate specific antibody. The beads may be lyophilized (freeze-dried) to allow for storage at 4° C. for several months without loss of binding affinity. These ready-made beads reduce the time necessary to execute the assay provided by the kit. In some embodiments, the beads may be lyophilized in the presence of 0.1 M ammonium biocarbonate buffer. In certain embodiments, the kit may include a control substrate that cannot be cleaved by the protease. In certain embodiments, the enrichment matrix of the kit may be provided in an immunosorbent support comprised of loose beads or a fixed column as described above.

According to some embodiments, the methods or kits provided herein may be used in a manual or automated format. In certain embodiments, the methods or kits may be used as a high-throughput detection system. In some embodiments, the methods or kits may be used as a high-throughput detection system for inhibitors of protease enzymatic activity. Such high-throughput detection systems are preferably automated for large-scale detection and testing, such as may be used in a diagnostic medical laboratory or in a manufacturing facility.

Definitions:

As used herein, the term "protease" refers to any enzyme that is capable of cleaving a peptide bond. For example, as shown in the examples below, collagenase, thermolysin, neutral protease, and dispase are bacterial proteases that are capable of cleaving a peptide bond of a protease substrate.

As used herein, the term "protease substrate," "peptide substrate," or "substrate" refers to any chemical, biochemical or biological species or compound that complexes with, reacts with, is capable of being modified by, or otherwise interacts with a protease having bioactivity. In certain embodiments, a protease substrate is a protein or peptide comprising an amino acid sequence comprising at least one protease cleavage site. Certain protease substrates may comprise one or more protease cleavage sites. For example, the protease substrate may comprise one or more collagenase cleavage sites.

The following examples are intended to illustrate various embodiments of the disclosure. As such, the specific embodiments discussed are not to be construed as limitations on the scope of the disclosure. It will be apparent to one skilled in the art that various equivalents, changes, and modifications may be made without departing from the scope of the disclosure, and it is understood that such equivalent embodiments are to be included herein. Further, all references cited in the disclosure are hereby incorporated by reference in their entirety, as if fully set forth herein.

EXAMPLES

Example 1: Synthesis of Protease Substrate

The amino acid sequence of the novel protease substrate 5FAMcollagenPPT is:

5-FAM-Ala-Gly-Gly-Pro-Leu-Gly-Pro-Pro-Gly-Pro-Gly-Gly-Lys-[DABCYL]-amide (i.e., SEQ ID: NO 2). A 5-carboxyfluorescein (5-FAM) was conjugated to the peptide's N-terminus, while a 4-((4-(Dimethylamino)phenyl)azo)benzoic acid (DABCYL) was bound to the epsilon side chain of the terminal lysine. The C-terminus is an amide group.

Synthesis of the protease substrate 5FAMcollagenPPT was designed and performed according to the general methods outlined in Kaplan 1998 with some modifications using Fmoc-Lys (dde)-OH and K (dabcyl). After the removal of the terminal Fmoc group, 5(6)-carboxyfluorescein was activated. The excess reagents were washed out with piperidine: DMF (1:4). The Lys (Dde) was deprotected using 2% hydrazine in DMF, washed with DMF and DCM and 4-dimethylaminoazobenzene-4'-carboxylic acid (dabcyl) was activated in the usual manner and coupled as any standard amino acid. The resin was washed and the peptide was cleaved from the resin by standard methods. The peptide was purified by HPLC as described previously and the sequence was confirmed by mass spectrometry (Kaplan 1998). The stock protease substrate was reconstituted in 100 mM TEA buffer at pH 8.0. It was then aliquoted and stored protected from light at −80° C. until used. The protease substrate is water soluble and can be stored at −80° C.

Example 2: Detection of Proteolytic Activity of Collagenases, Neutral and Pancreatic Proteases A robust and highly sensitive fluorogenic assay was developed to measure the activity of bacterial proteases using the novel, synthetic, fluorogenic protease substrate, 5FAMcollagenPPT. A Fluorescence Resonance Energy Transfer (FRET) based assay was used to monitor changes in fluorescence of the 5FAMcollagenPPT protease substrate upon enzymatic cleavage of the protease substrate by a variety of enzymes. The kinetic parameters for the protease substrate with different enzymes were assessed with and without $CaCl_2$, Zinc, and EGTA. The cleavage of the protease substrate using bacterial and pancreatic proteases was also tested.

Materials and Methods

Chemicals, Reagents, and Enzymes.

Chemicals, including trypsin, chymotrypsim, elastase, 4-(dimethylaminoazo)benzene-4-carboxylic acid (dabcyl), 5(6)-carboxyfluorescein, N,N,N',N'-Tetrakis(2-pyridinylmethyl)-1,2-ethanediamine (TPEN), $ZnCl_2$, $ZnSO_4$, $NaSO_4$, triethanolamine (TEA), ethylenediaminetetraacetic (EDTA), ethylene glycol-bis(β-aminoethyl ether)-N,N,N',N'-tetraacetic acid (EGTA), and $CaCl_2$ were purchased from Sigma-Aldrich (Saint Louis, Mo.). Highly purified collagenase class I, II and thermolysin samples were kindly provided by Roche Diagnostics (Roche Diagnostics, Roche Applied Science, Indianapolis, Ind., USA). Neutral Protease was purchased from Serva (SERVA Electrophoresis GmbH, Heidelberg, Germany).

FRET Assay for Enzymatic Reaction.

The reaction kinetics between enzymes and newly synthesized 5FAMcollagenPPT protease substrate were evaluated using FRET. Briefly, donor and quencher (dabcyl) molecules were attached to corresponding amino acids as described above to synthesize the fluorogenic protease substrate. After cleavage of the substrate by the enzymes, fluorophore quenching diminished due to the separation of donor and quencher moieties (Weimer 2006; Cummings 2002; Matayoshi 1990). As a result, the donor fluorescence increased dramatically upon substrate cleavage, which was measured at excitation 485 nm and emission at 535 nm. The enzymatic reaction was performed in a 96-well round bottom black plate (Costar ID#3915, Corning, N.Y.). Briefly, 190 μl of substrate with a final concentration of 5-80 μM and 10 μl of specific enzyme samples were added to each well, creating a final volume of 200 μl/well. A blank sample was used that contained only substrate with no enzyme sample. In addition, enzyme samples were boiled for 5 min at 80° C. and used as a control. The plate was incubated (light protected) for 1 hour at 22° C. and the reaction was stopped by adding 50 μl of 40 mM EDTA solution (pH 8.0). The fluorescence was read at excitation 485 nm and emission 535 nm using the Tecan Magellan V 6.5 Genios plate reader (Tecan Systems, Inc., San Jose, Calif., USA). Microsoft excel was used to further extrapolate the data.

Enzyme Kinetic Assay.

The Michaelis-Menten Model of enzyme kinetics and Lineweaver-Burk plot and equation were used to establish the rate of the enzymatic reaction in relationship to the substrate using known substrate concentrations (Bagramyan 2008). The Michaelis-Menten model was chosen for analysis as it allows for the comparison of different enzyme enhancers and the effect of these activators on the enzymatic reaction (Diaz 2015). The $V_{max}$ and $K_m$ values were calculated using GraphPad Prism. The 5FAMcollagenPPT substrate concentrations used were: 5, 10, 20, 40, 60 and 80 μM. The concentrations of the tested enzyme were: 0.45 μg/ml for Collagenase I, 0.3 μg/ml for Collagenase II, 17 μg/ml for Thermolysin, and 20 μg/ml for Neutral Protease. The enzymatic kinetics of the 5FAMcollagenPPT protease substrate and enzymes were tested under following conditions: i) absence and presence of $CaCl_2$ (4.14 mM), $ZnSO_4$ (16.7 μM), $ZnCl_2$ (16.7 μM), $NaSO_4$ (16.7 μM), and chelating agents EGTA (25, 50, 100 mM); ii) change of pH (pH 6.0-8.0); iii) scaling-up concentrations (2.5, 5, 10 μg/ml) of pancreatic endogenous proteases (trypsin, chymotrypsin and elastase) were also used to examine the efficiency to cleave peptide substrate.

Statistical Analysis.

GraphPad Prism (GraphPad Software 6.0, La Jolla, Calif., USA) was used for analyzing the data and generating the graphs. Both non-linear Michaelis-Menten and linear Lineweaver-Burk plots were used for the enzyme kinetics study. Kinetic parameters $V_{max}$ and $K_m$ were obtained from the Michaelis-Menten model by plotting the reaction velocity at different concentration of peptide substrate. Non-linear Michaelis-Menten curves for the enzymatic reaction in the presence and absence of $CaCl_2$ were compared using Prism. All samples were run in duplicate, and results are reported as average±standard error of the mean (SEM). One-way or two-way ANOVA analysis followed by Tukey's multiple comparisons test was used to conduct multiple variable comparisons when applicable. Differences in data were considered significant when P values were less than 0.05.

Results

Effect of $CaCl_2$ on Protease Substrate Cleavage.

Figure 3A:
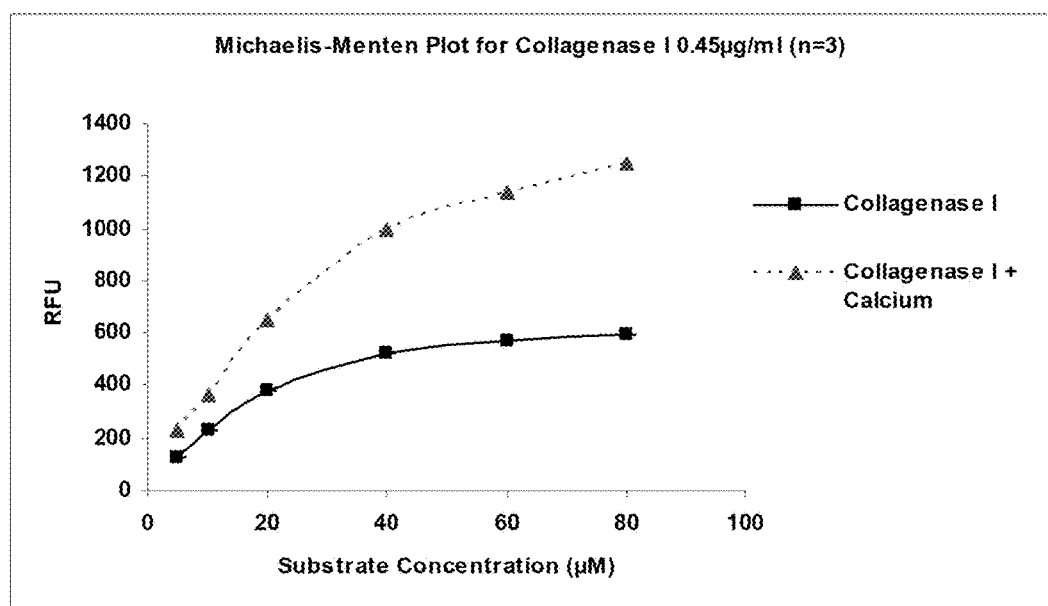
FIGS. 3A-H illustrate the proteolytic activity of collagenases, thermolysin, and neutral proteases using the protease substrate 5FAMcollagenPPT. $K_M$ and $V_{max}$ values for the proteases with and without 4.14 mM calcium respectively were: collagenase I: $K_M$ 32.93/38.06 and $V_{max}$ 1008.158/1704.72; collagenase II: $K_M$ 29.74616/24.07228 and $V_{max}$ 3354.43/3243.942; thermolysin: $K_M$ 24.76/30.4 and $V_{max}$ 25.47/23.7; and neutral protease: $K_M$ 45.14/74.08 and $V_{max}$ 29.28/20.04; where $K_M$=µM and $V_{max}$=RFU/min/µg.
Figure 3B:
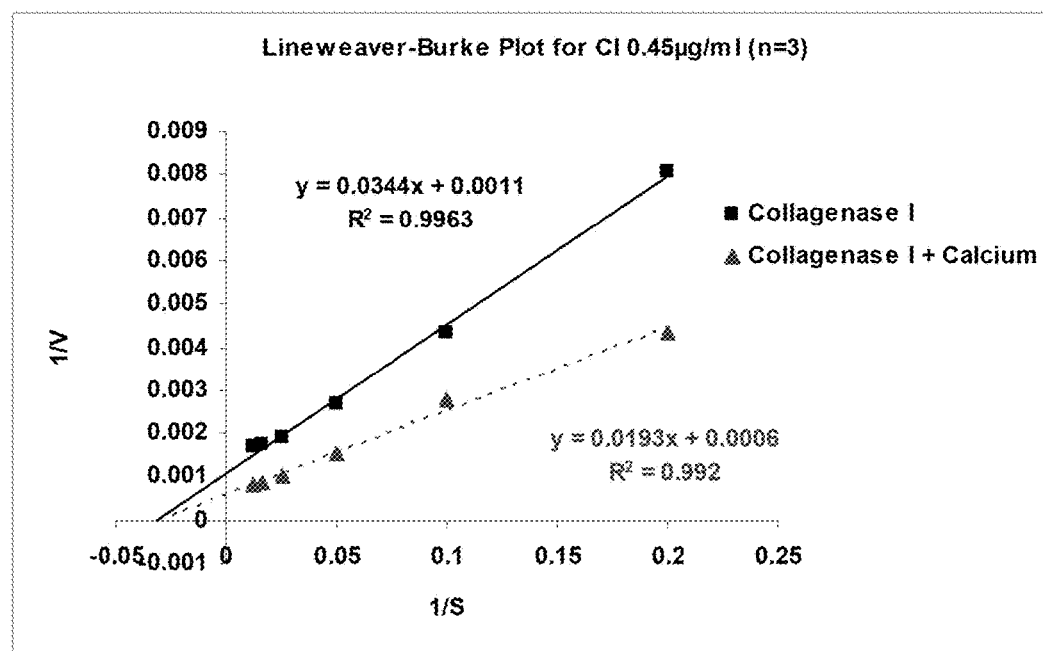
Figure 3C:
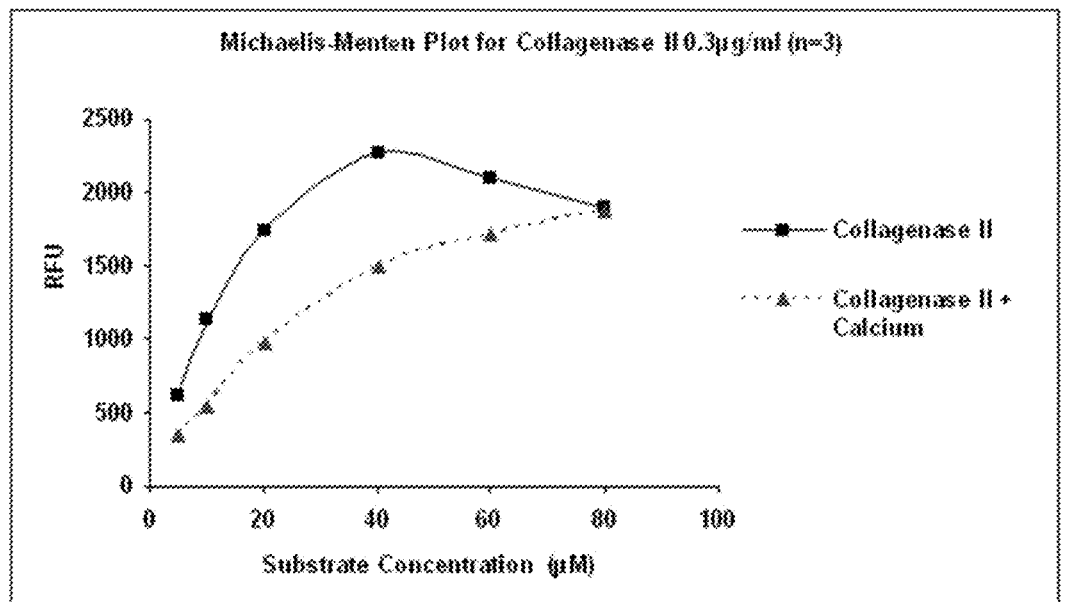
Figure 3D:
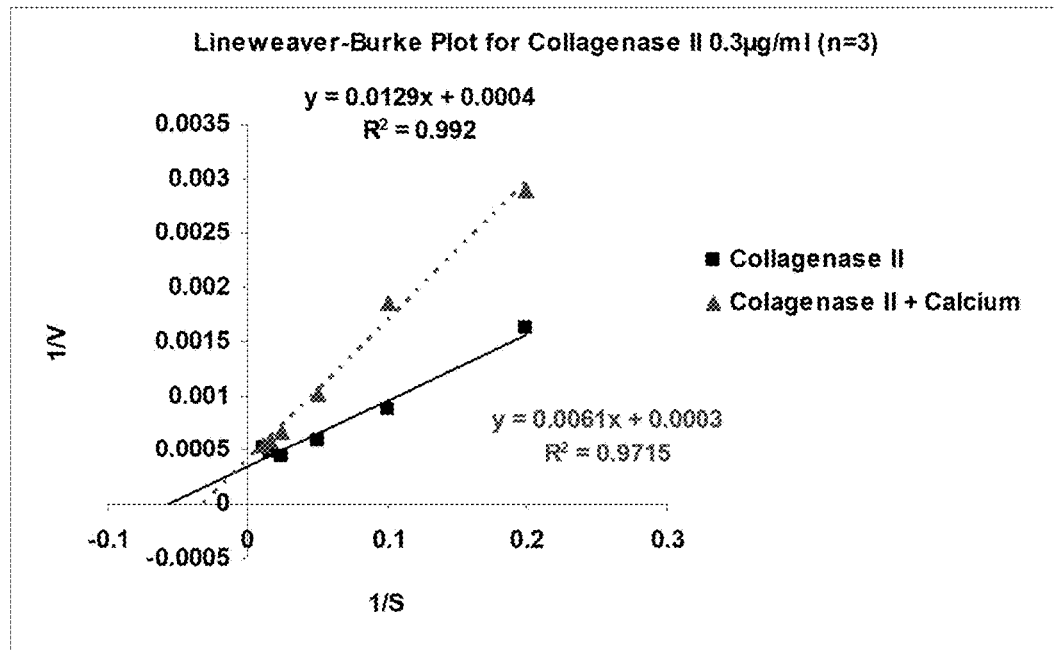
Figure 3E:
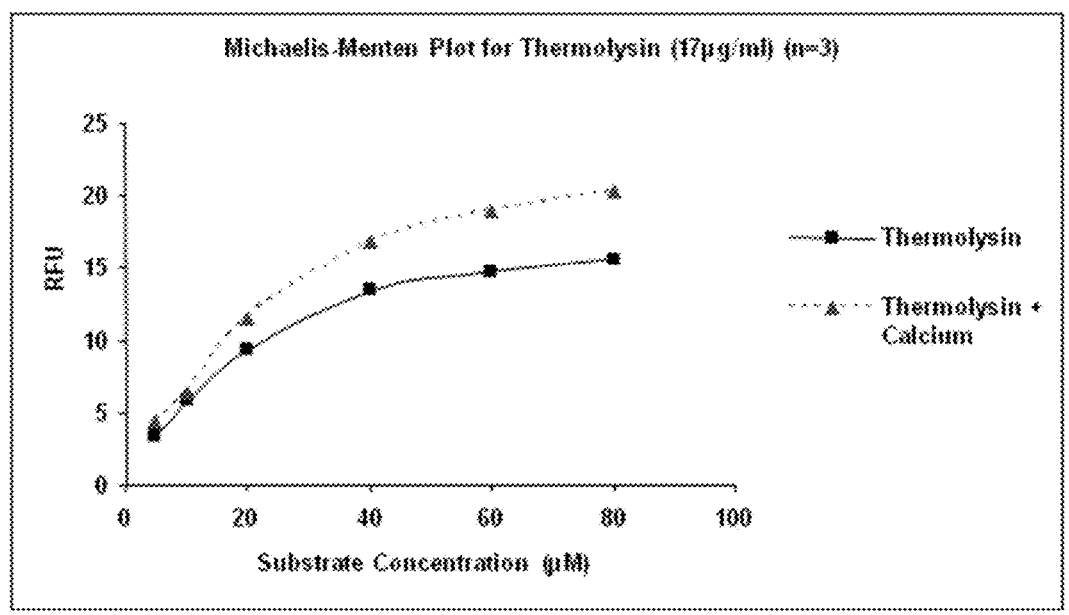
Figure 3F:
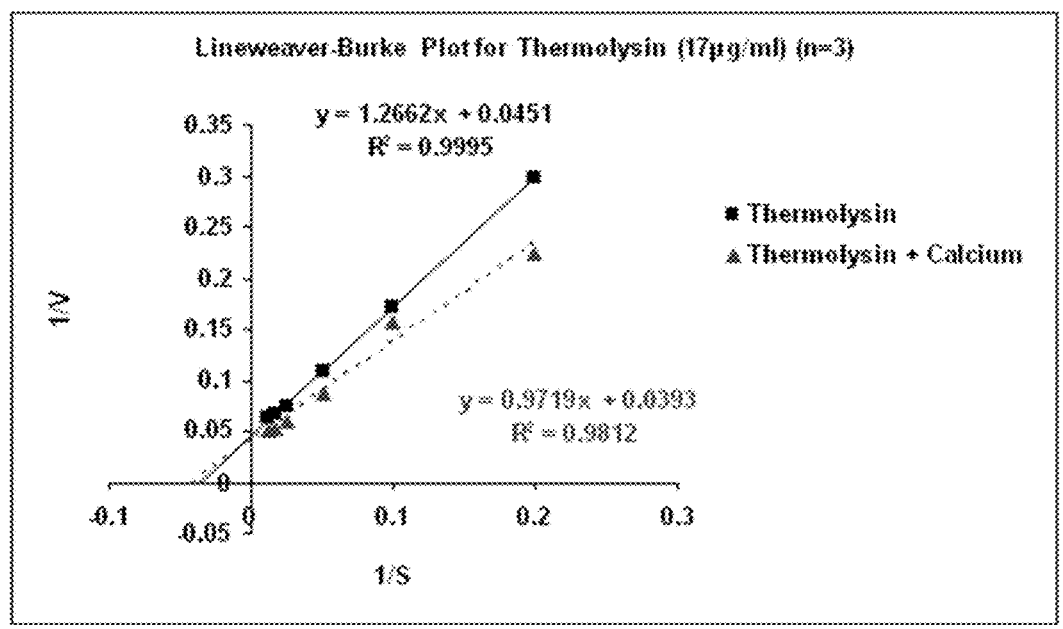
Figure 3G:
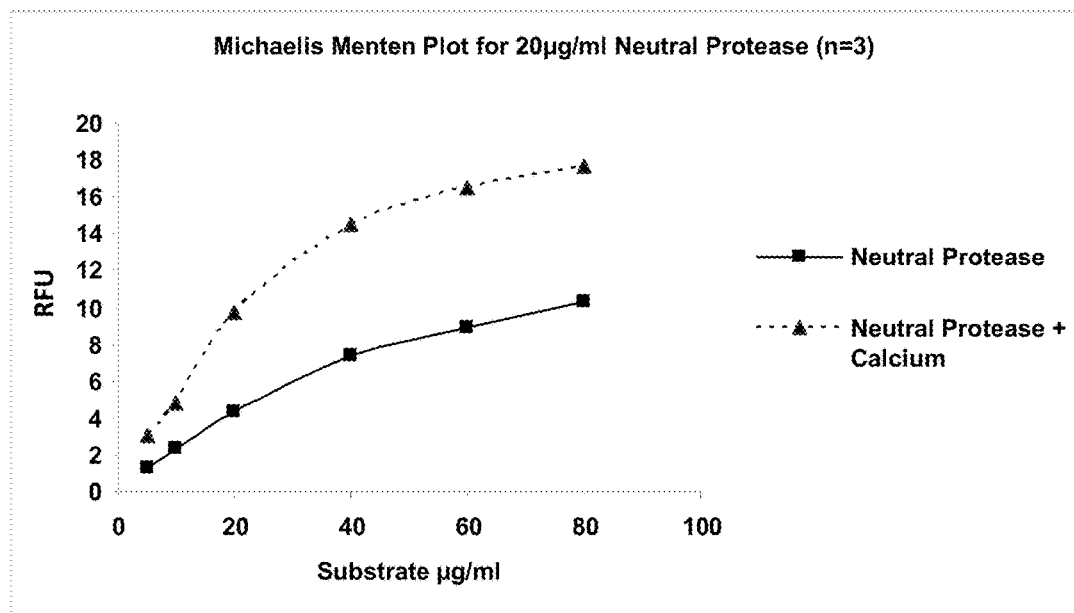
Figure 3H:
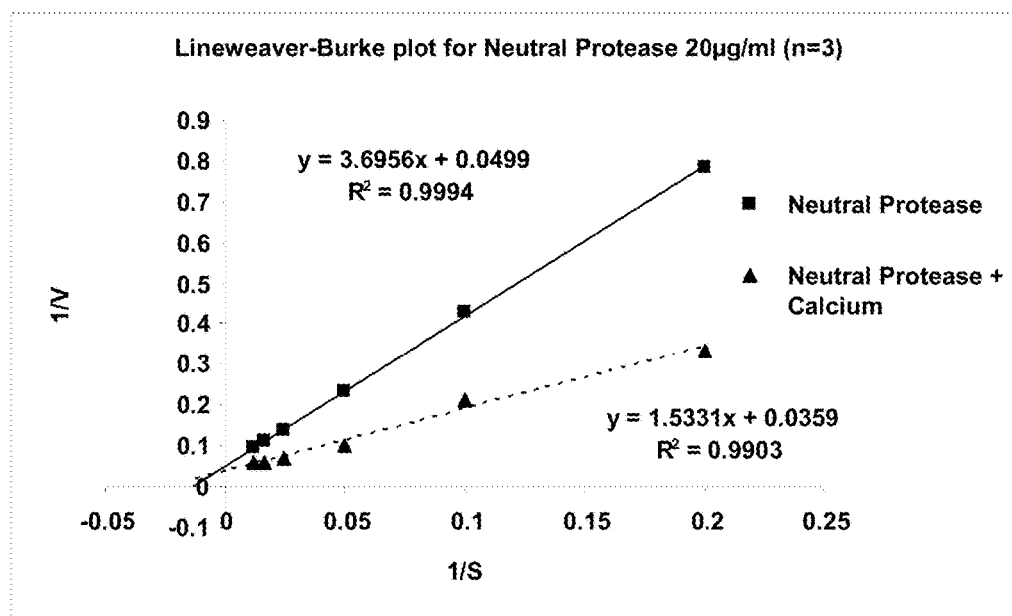

FIGS. 3A-H demonstrate the utility of this fluorogenic assay in determining the enzymatic activities of Class I collagenase ("collagenase I"; FIGS. 3A and 3B), Class II collagenase ("collagenase II"; FIGS. 3C and 3D), thermolysin (FIGS. 3E and 3F), and neutral protease (FIGS. 3G and 3H). The corresponding $K_m$ and $V_{max}$ values for the protease substrate 5FAMcollagenPPT and the different proteases with and without 4.14 mM calcium are provided in Table 5.

TABLE 5

Kinetic parameters ($K_m$ and $V_{max}$) for the protease substrate 5FAMcollagenPPT with the respective proteases.

|  | with 4.14 mM calcium*** | | without calcium | |
| --- | --- | --- | --- | --- |
|  | *$K_m$ | **$V_{max}$ | $K_m$ | $V_{max}$ |
| collagenase I | 32.93 | 1008.158 | 38.06 | 1704.72 |
| collagenase II | 29.74616 | 3354.43 | 24.07228 | 3243.942 |
| thermolysin | 24.76 | 25.47 | 30.4 | 23.7 |
| neutral protease | 45.14 | 29.28 | 74.08 | 20.04 |

*$K_m$ = μM
**$V_{max}$ = RFU/min/μg
***See Gray et al, 1984.

Figure 4A:
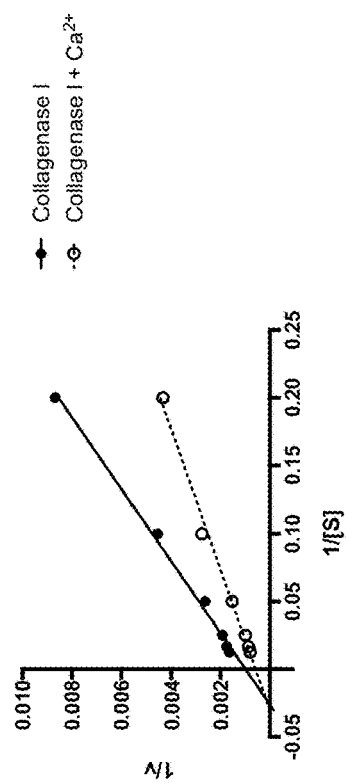
Figure 4B:
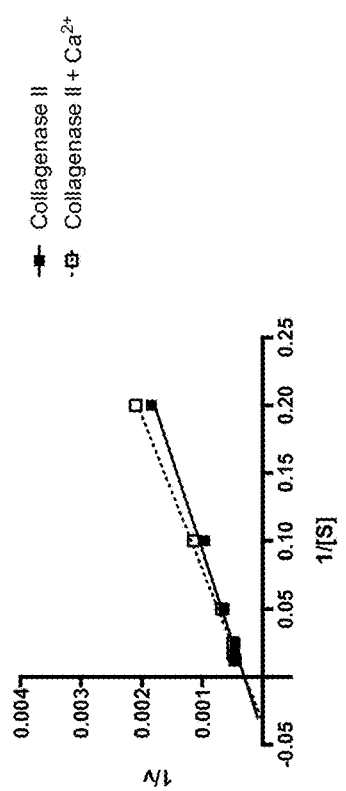
Figure 4C:
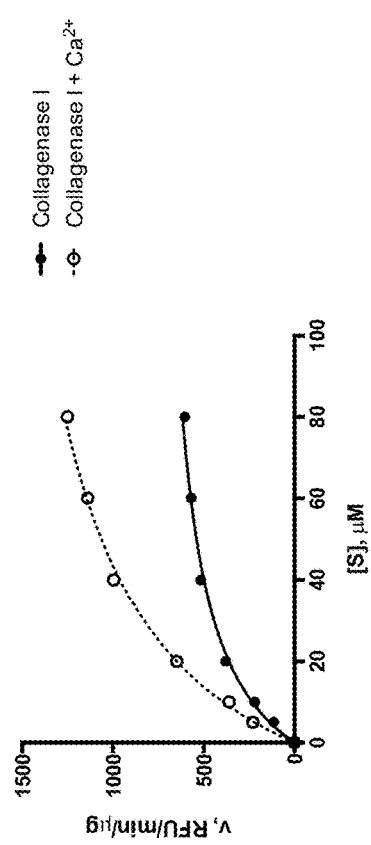
Figure 4D:
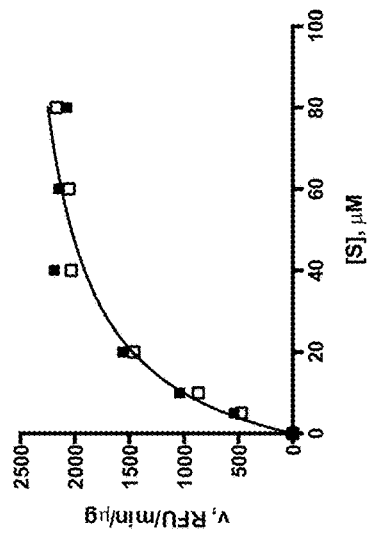
Figure 6A:
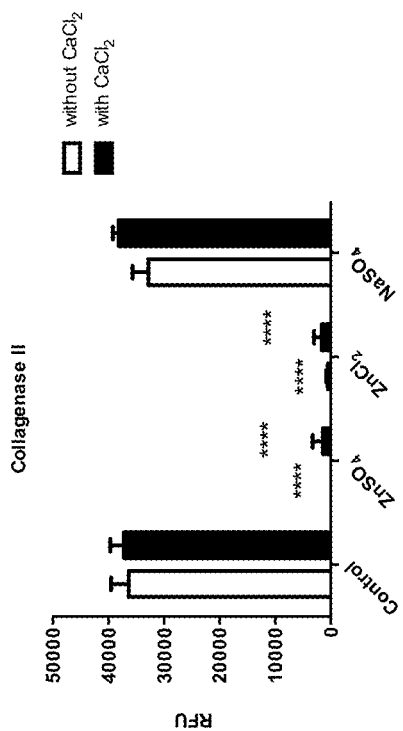
FIGS. 6A-D illustrate the effect of zinc on enzyme cleavage activity. The enzymes tested were Collagenase I (FIG. 6A), Collagenase II (FIG. 6B), Thermolysin (FIG. 6C), and Neutral Protease (FIG. 6D). The protease substrate 5FAMcollagenPPT used in this experiment was at a concentration of 20 µM. The experiment was performed three times and values were expressed as mean±standard error of mean (SEM). *p<0.05, p<0.01, and **p<0.0001 compared to control. Black bars indicate experiments performed without $CaCl_2$ and white bars indicate experiments performed with $CaCl_2$.
Figure 6B:
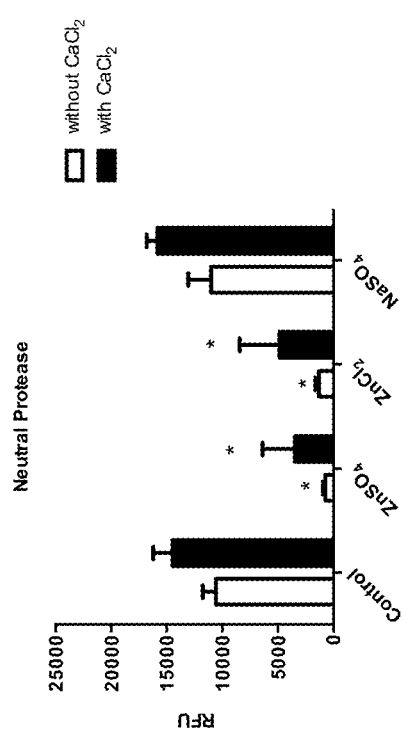
Figure 6C:
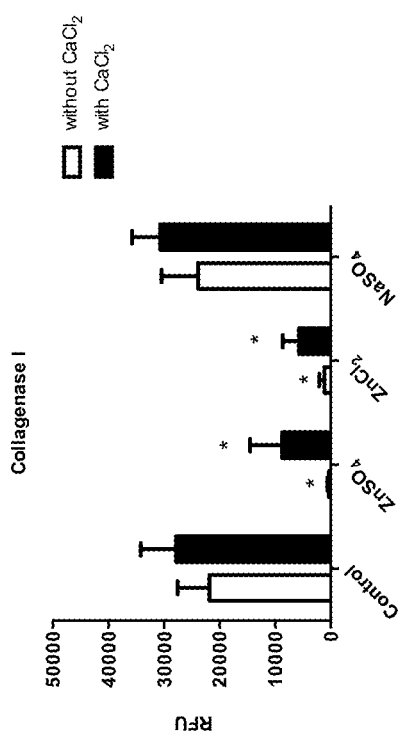
Figure 6D:
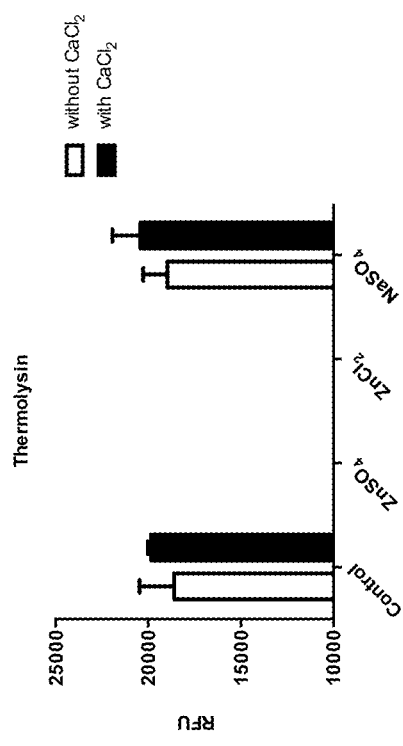

Additional experiments regarding the effect of $CaCl_2$) on enzyme activity were performed and results are presented in FIGS. 4A-H. FIGS. 4A-H show that the kinetics of enzyme activity increased the fluorescent intensity (relative fluorescence units, RFU) in a substrate-dependent manner. FIGS. 4A, 4B, 4G, and 4H demonstrate that the reaction of 0.45 μg/ml of Collagenase I (n=3, FIGS. 4A, 4B) and 20 μg/ml of Neutral Protease (n=3, FIGS. 4G, 4H) were significantly enhanced in the presence of $CaCl_2$) (Collagenase I, p<0.0001; Neutral Protease, p<0.0001). However, as shown in FIGS. 4C, 4D, 4E, and 4F, the reaction curves of both 0.3 μg/ml of Collagenase II (n=3, FIGS. 4C, 4D) and 17 μg/ml thermolysin (n=3, FIGS. 4E, 4F) did not change significantly when $CaCl_2$ was added (Collagenase II, p=0.490; Thermolysin, p=0.239). This was reflected by the occurrence of shared non-liner fit line between the conditions of presence and absent of $CaCl_2$ (FIGS. 4C, E). FIG. 5 shows $V_{max}$ and $K_m$ values obtained from the Michaelis-Menten plot. The effect of $CaCl_2$ on enzyme activity has rarely been reported with experimental evidence. Only for Collagenase I and Neutral Protease was the cleavage of the 5FAMcollagenPPT protease substrate enhanced significantly in the presence of $CaCl_2$). However, it is important to understand that $CaCl_2$ should be regularly used during the digestion of pancreatic tissue since these aforementioned enzymes are the essential component of the current enzyme combination for islet isolation.

The protease substrate 5FAMcollagenPPT displayed surprisingly high sensitivity and specificity as demonstrated by the documented $K_m$ and $V_{max}$ values (see Table 5 and FIG. 5). This is in contrast to results obtained with a previously published peptide, Peptide 1 (Saikumari, 2008; see FIG. 2). Furthermore, the protease substrate 5FAMcollagenPPT was cleaved by thermolysin (see FIGS. 3E, 3F, 4E, and 4F) while the previously published peptide, Peptide 1, is not cleaved by thermolysin (see FIG. 3 of Saikumari, 2008).

Effect of zinc on protease substrate cleavage. The effect of zinc ions on enzyme activity was investigated using a solution of $ZnSO_4$ (16.7 µM) or $ZnCl_2$ (16.7 µM). $NaSO_4$ (16.7 µM) was used as a control to compare the Zn effect to the influence of Na or $SO_4$ ions. The reaction was conducted in the presence and absence of $CaCl_2$ (4.14 mM). The 5FAMcollagenPPT substrate used in this experiment was used at a concentration of 20 µM. As shown in FIGS. 6A-D, for all the four enzymes tested, the measured RFU was significantly decreased by adding either $ZnSO_4$ or $ZnCl_2$ regardless of presence or absence of $CaCl_2$). The significant differences were found not only between zinc contained chemical and control groups, but also between zinc contained chemical and $NaSO_4$. These results clearly show that the enzymatic cleavage was significantly inhibited in the presence of zinc. Previous studies have shown that collagenase enzymes bind to islets post culture and attributed this to be the cause of the deteriorating effect resulting in islet loss (Balamurugan 2006). Additional data suggest that collagenase activity was not detected in culture media taken from islet samples post culture (data not shown). This result may be explained by the fact that the presence of zinc culture medium may have interfered with the outcome of the collagenase activity using this assay.

Effect of EGTA on Protease Substrate Cleavage.

Figure 7:
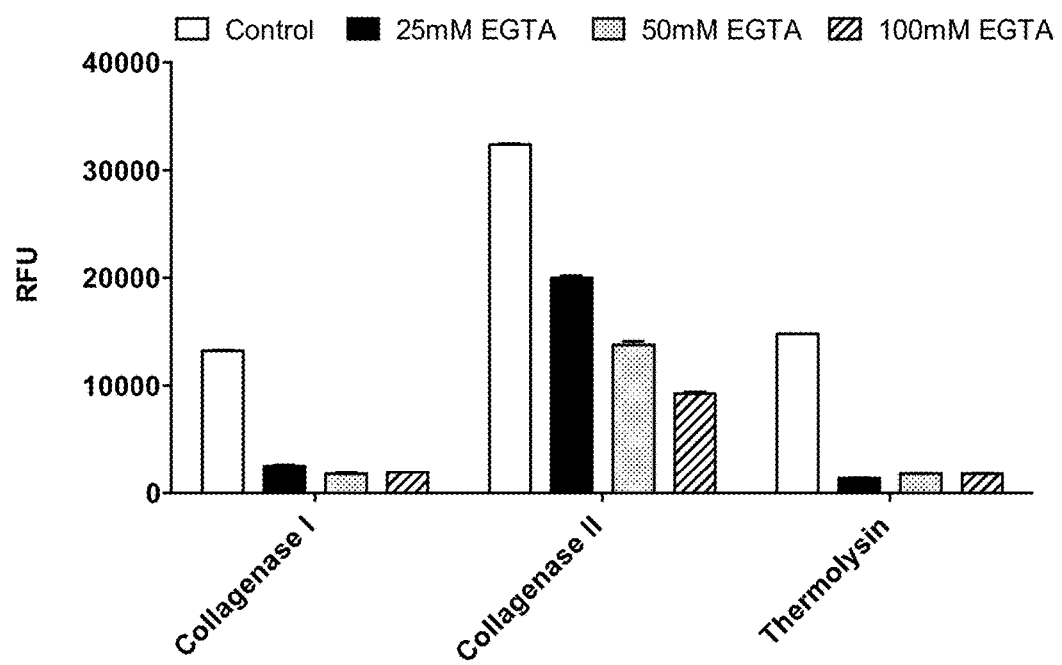
FIG. 7 shows the effects of chelating agent EGTA on enzymatic cleavage activity. There were significant differences of RFU levels between the controls and varied concentrations of EGTA (25, 50, and 100 mM) for Collagenase I (0.45 µg/ml), Collagenase II (0.3 µg/ml), and thermolysin (17 µg/ml) (****p<0.0001). The assay was conducted using a 5FAMcollagenPPT protease substrate concentration of 20 µM.

Increasing concentrations of EGTA (25 mM, 50 mM, and 100 mM) were used to study the effect of chelating agents on the enzymatic activity (FIG. 7). There were significant differences of RFU levels between the controls and various concentrations of EGTA (25, 50, and 100 mM) for Collagenase I (0.45 µg/ml), Collagenase II (0.3 µg/ml), and Thermolysin (17 µg/ml) (FIG. 7, p<0.0001). Results showed that the presence of EGTA, which is a mono calcium chelating agent, eliminated the effect of $CaCl_2$. These results emphasize the importance of $CaCl_2$ during digestion process.

Effect of pH and Culture Time/Temperature on Enzyme Activity.

Figure 8:
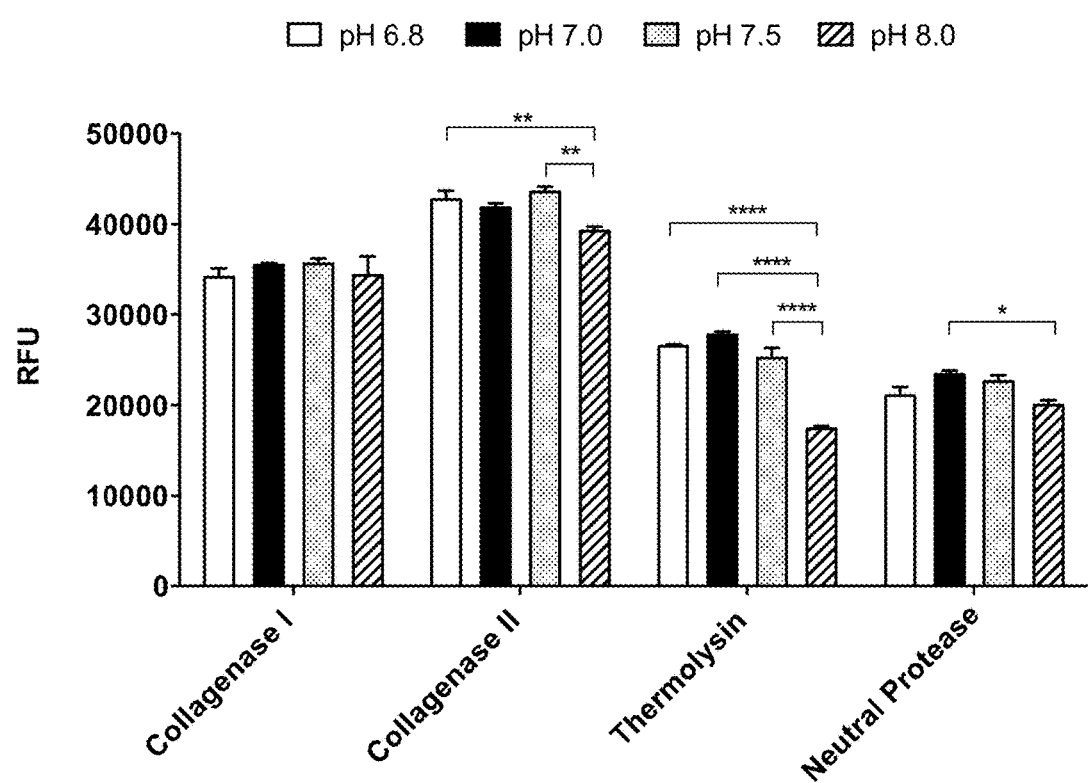
FIG. 8 shows the effects of pH on enzymatic cleavage activity. There were significant differences between different levels of pH for all of the enzymes except Collagenase I. For Collagenase II, the reaction was significantly inhibited at pH 8.0, compared with pH 6.8 and pH 7.5 (p<0.01). With regard to Thermolysin, the reaction was significantly inhibited at pH 8.0 when compared to all other pH conditions (**p<0.0001). For Neutral Protease, there was significant difference between pH 7.0 and pH 8.0 (*p<0.05). The assay was conducted using a 5FAMcollagenPPT substrate concentration of 20 µM.

The influence of pH on the enzyme activity was also tested. The results showed that for all the enzyme activities were influenced by pH except Collagenase I (FIG. 8). For Collagenase II, the reaction was significantly inhibited at pH 8.0, as compared with pH 6.8 and pH 7.5 (p<0.01). With regard to Thermolysin, the reaction was significantly inhibited at pH 8.0 when compared to all other pH conditions (p<0.0001). For Neutral Protease, there was significant difference between pH 7.0 and pH 8.0 (p<0.05). pH value of the reaction buffer affects the enzyme activity. Within the four sets of pH conditions in this experiment, only the pH 8.0 impaired the enzyme activity. The enzyme activity was not affected at pH 6.8, pH 7.0, and pH 7.5. The range of pH 6.8-7.5 is relatively physiological and usually expected during islet isolation to eliminate the detrimental effect of non-optimal pH levels. Therefore, it is suggested that pH of any digestion solution used for islet isolation should keep within the range of 6.8-7.5.

Cleavage of Protease Substrate Using Pancreatic Proteases.

Figure 9:
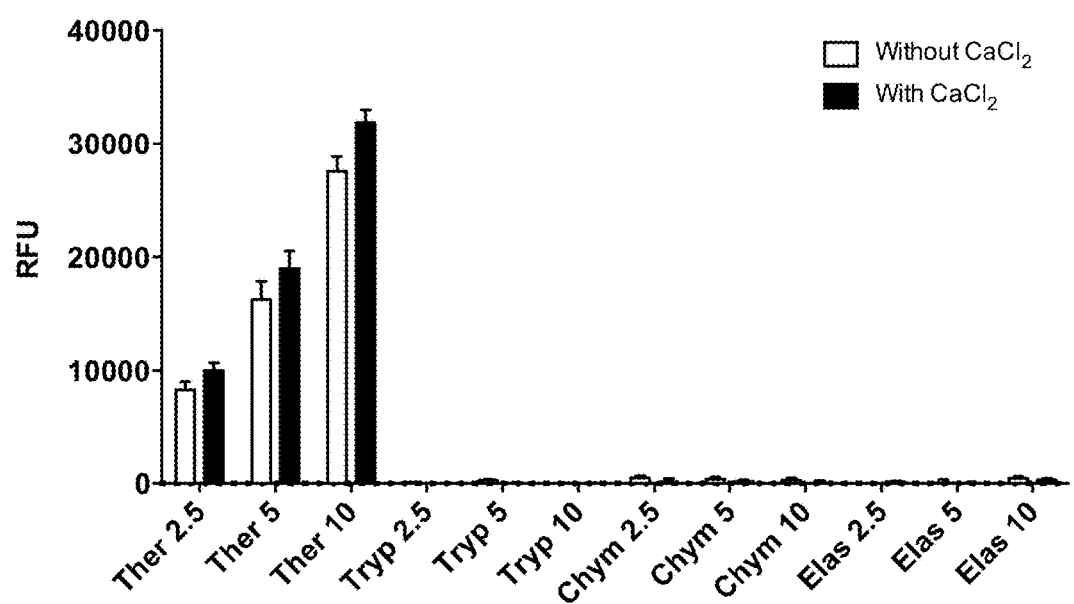
FIG. 9 shows the proteolytic activity of thermolysin, trypsin, chymotrypsin, and elastase. The protease substrate 5FAMcollagenPPT was not cleaved by endogenous mammalian pancreatic proteases such as trypsin, chymotrypsin, and elastase, but was cleaved by the bacterial protease, thermolysin. All enzymes (thermolysin, trypsin, chymotrypsin, and elastase) were tested at 2.5 µg/ml, 5 µg/ml and 10 µg/ml. The white bar represents the experiment performed without calcium and the black bar represents the experiment performed with calcium. Thermolysin demonstrated a dose dependent cleavage of peptide substrate both in the presence and absence of 4.14 mM $CaCl_2$). All three pancreatic proteases showed no activity compared to thermolysin using (2.5, 5, 10 µM), regardless of the presence of $CaCl_2$) or not (****p<0.0001). The peptide substrate was tested at a concentration of 50 µM (n=3). Error bars were determined using the standard error of the mean (SEM).

The fluorogenic assay was also used to further test whether the customized 5FAMcollagenPPT protease substrate could be used specifically for testing the cleavage effect of enzymes used for human islet isolation, but not for any other universal protease. Pancreatic endogenous proteases were used to react with the 5FAMcollagenPPT protease substrate under the same conditions that are used for testing the enzymes for islet isolation. Because all the bacterial enzymes (collagenase I, collagenase II, thermolysin, and neutral protease) were shown to cleave the protease substrate, thermolysin was used to compare with the three endogenous pancreatic proteases (trypsin, chymotrypsin, and elastase). The results showed that thermolysin demonstrated a dose-dependent cleavage of 5FAMcollagenPPT protease substrate both in the presence and absence of 4.14 mM $CaCl_2$. However, all three pancreatic proteases (trypsin, chymotrypsin, and elastase) showed significantly diminished reactivity compared to thermolysin at all the concentrations tested (2.5, 5, 10 µM), regardless of the presence of $CaCl_2$ or not (p<0.0001, FIG. 9). This result showed that the synthesized 5FAMcollagenPPT protease substrate was specially cleaved by the enzymes, but not by the endogenous pancreatic proteases released during digestion of pancreatic tissue. It has been reported that proteases in pancreatic tissue degrade the extracellular matrix molecules such as proteoglycans and glycoproteins (Voss 1996). However, the collagenase used for islet isolation takes action on the collagenase binding site on collagen fibrils (Johnson 1996). These experiments showed that the protease substrate 5FAMcollagenPPT was specific to collagenase and bacterial neutral proteases, but was not cleaved in the presence of the pancreatic proteases trypsin, chymotrypsin, and elastase. Therefore, the novel protease substrate 5FAMcollagenPPT is useful for islet cell preparation.

Using the novel protease substrate 5FAMcollagenPPT, this fluorogenic assay can also be used to determine the activity of other bacterial enzymes such as neutral protease and dispase, which are used for tissue dissociation.

Example 3: Additional Experiments Detecting Proteolytic Activity

Figure 10A:
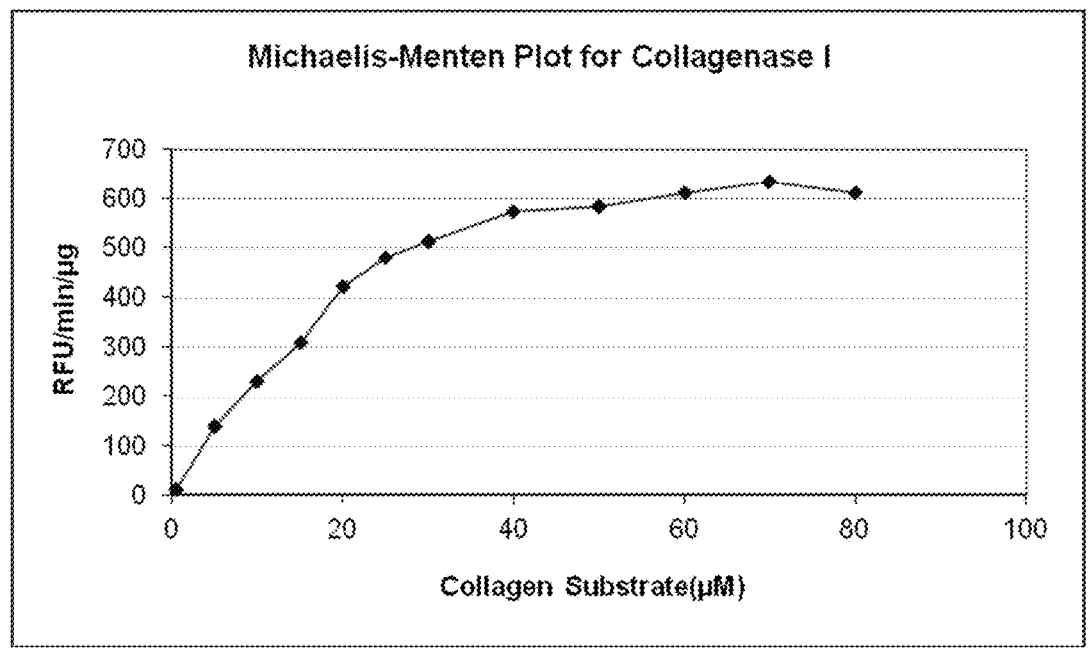
FIGS. 10A-H illustrate the proteolytic activity of bacterial collagenases and bacterial neutral proteases using the protease substrate 5FAMcollagenPPT. The $K_M$ and $V_{max}$ values for the different proteases were: collagenase I: $K_M$ 28.18 and $V_{max}$ 909; collagenase II: $K_M$ 24.5 and $V_{max}$ 5000; and thermolysin: $K_M$ 34.6 and $V_{max}$ 24.6; where $K_M$=µM and $V_{max}$=RFU/min/µg.
Figure 10B:
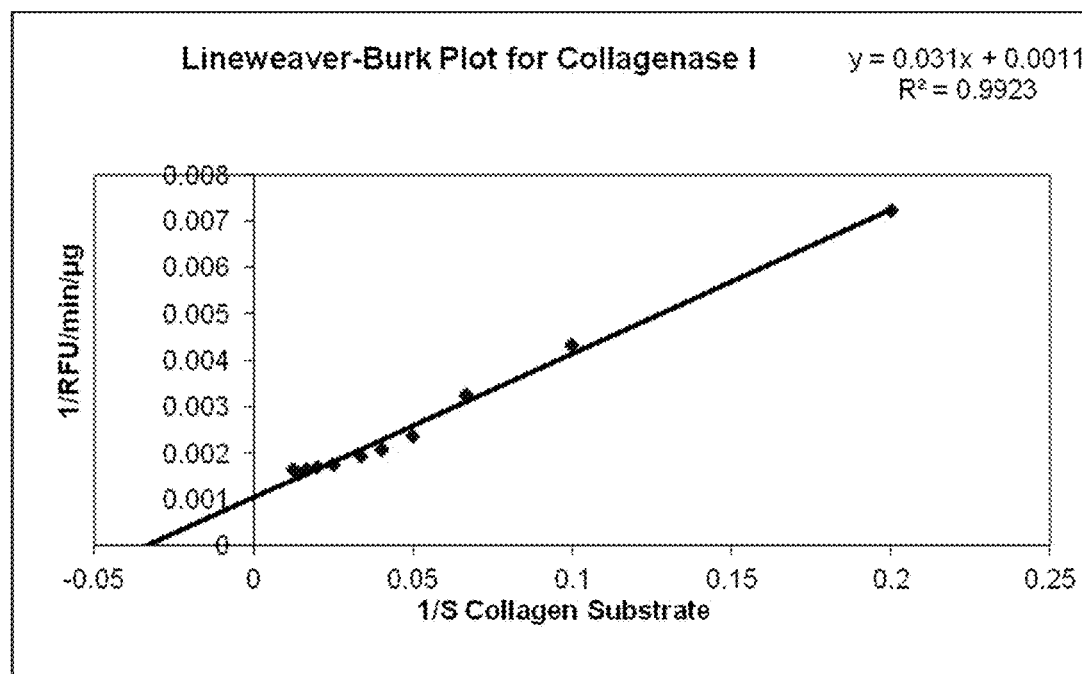
Figure 10C:
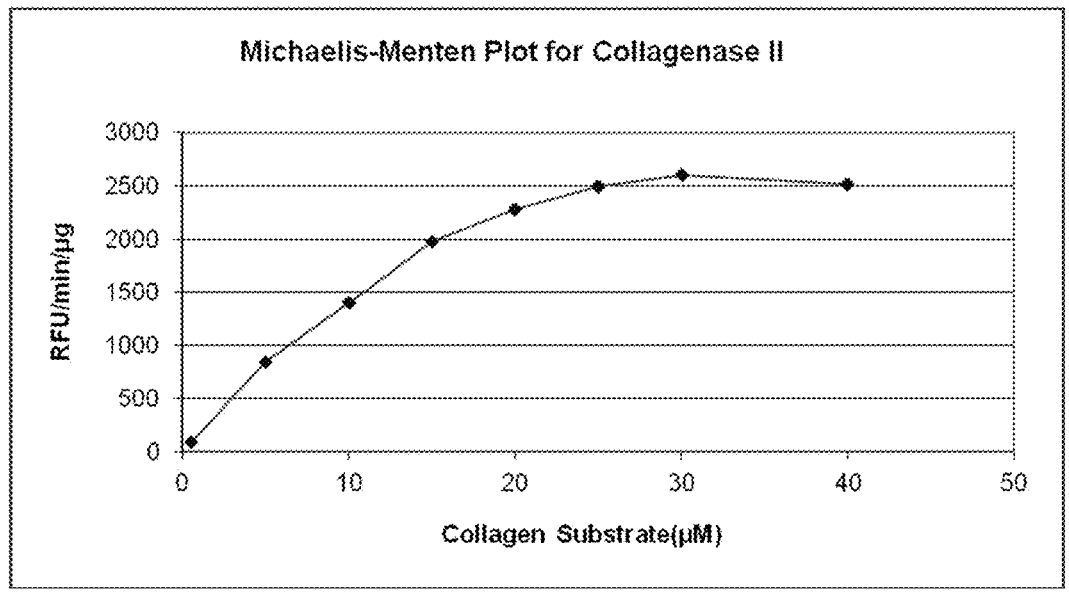
Figure 10D:
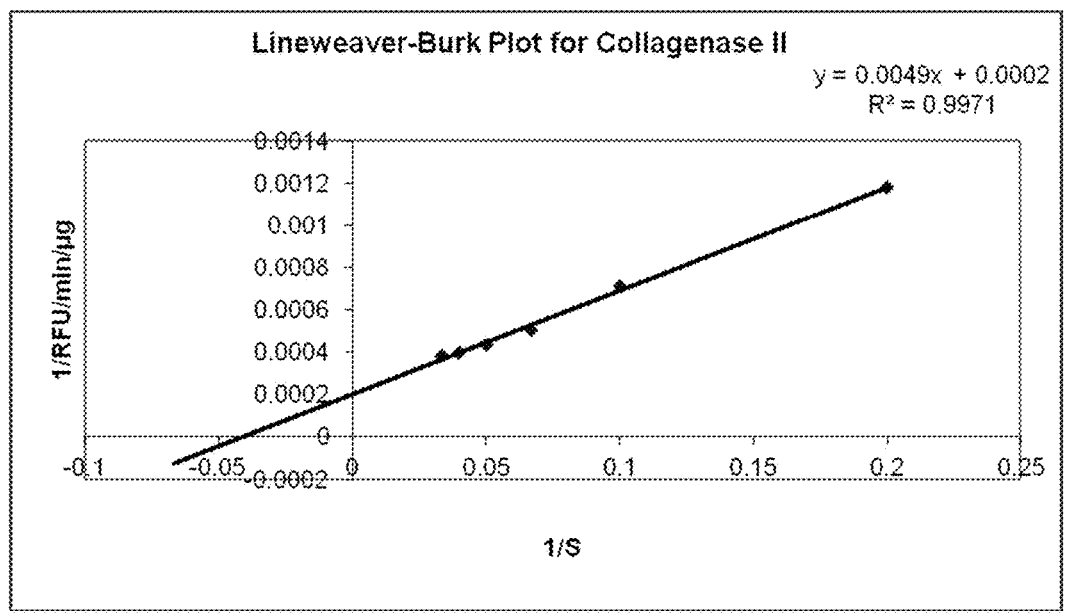
Figure 10E:
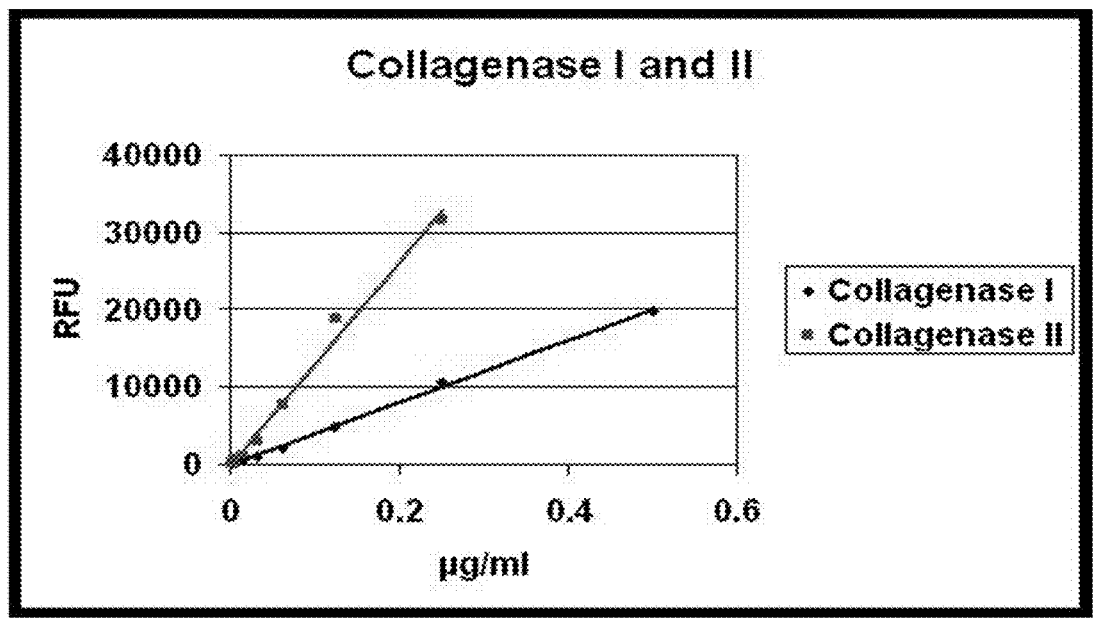
Figure 10F:
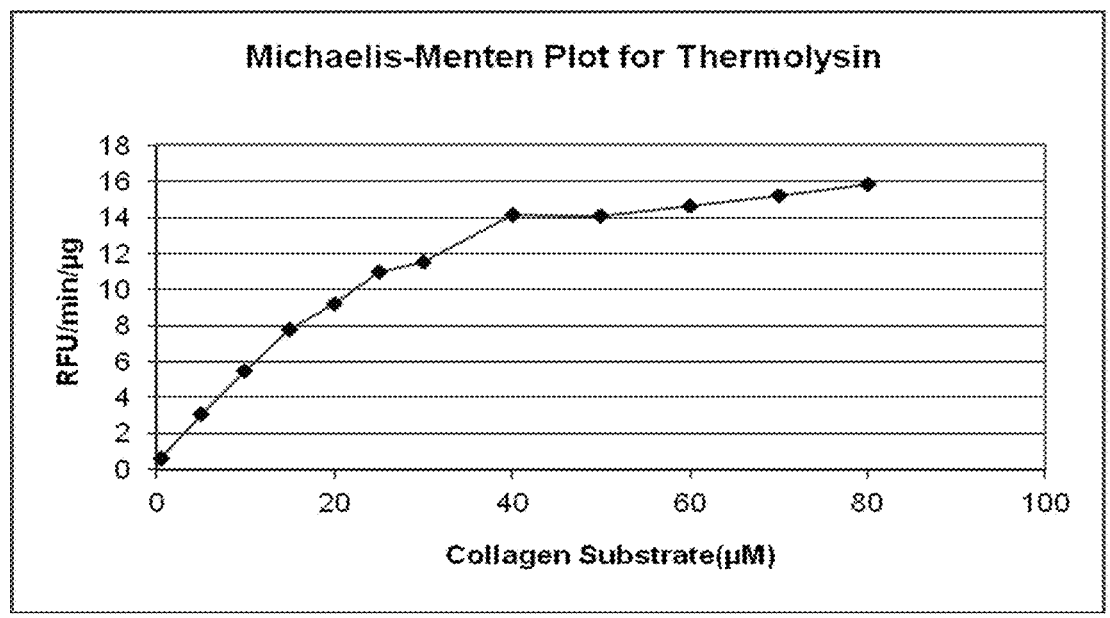
Figure 10G:
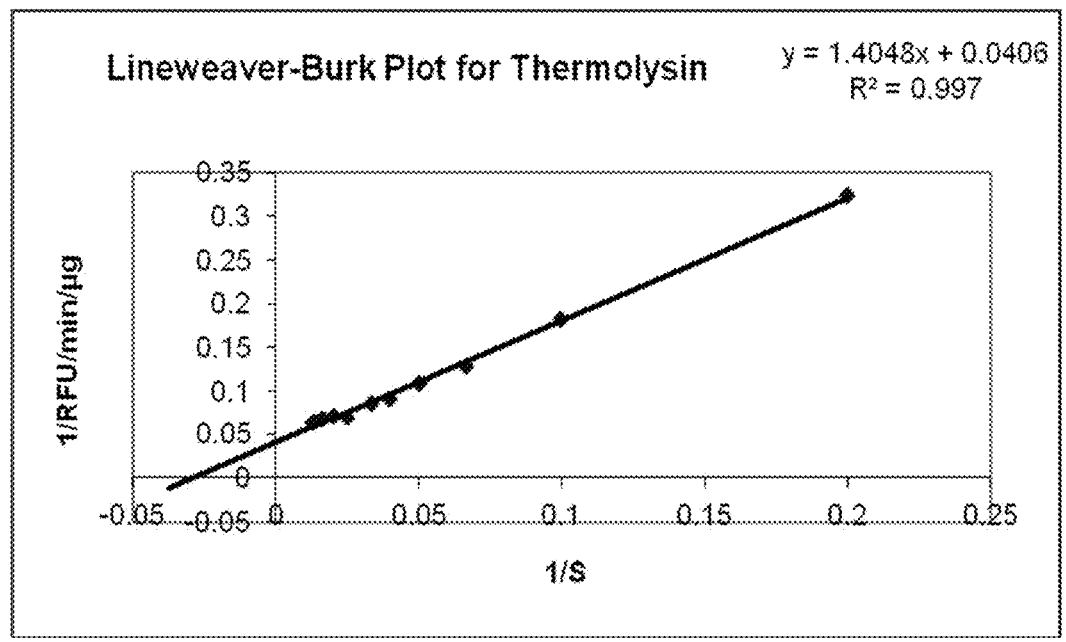
Figure 10H:
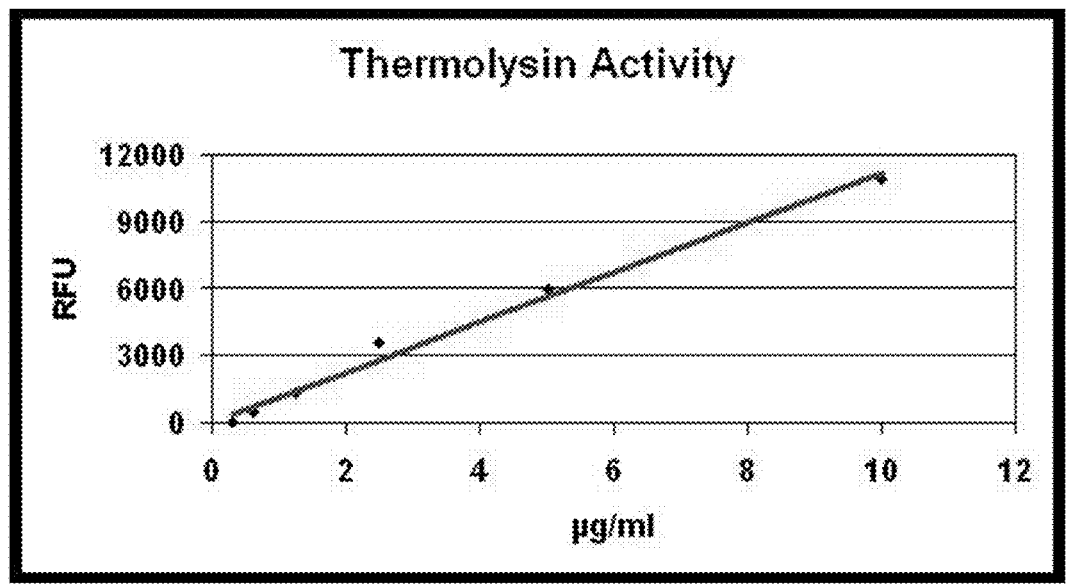

The novel fluorogenic protease substrate 5FAMcollagenPPT was used to precisely determine the activities of collagenase I (FIGS. 10A, 10B, and 10E), collagenase II (FIGS. 10C, 10D, and 10E), and thermolysin (FIGS. 10F, 10G, and 10H). The assay was performed as described in Example 2. The corresponding $K_m$ and $V_{max}$ values for the protease substrate 5FAMcollagenPPT and the different proteases are provided in Table 6.

TABLE 6

Kinetic parameters ($K_m$ and $V_{max}$) for the protease substrate, 5FAMcollagenPPT with the respective proteases.

| | $K_m$ | $V_{max}$ |
|---|---|---|
| collagenase I | 28.18 | 909 |
| collagenase II | 24.5 | 5000 |
| thermolysin | 34.6 | 24.6 |

*$K_m$ = µM
**$V_{max}$ = RFU/min/µg

Figure 11:
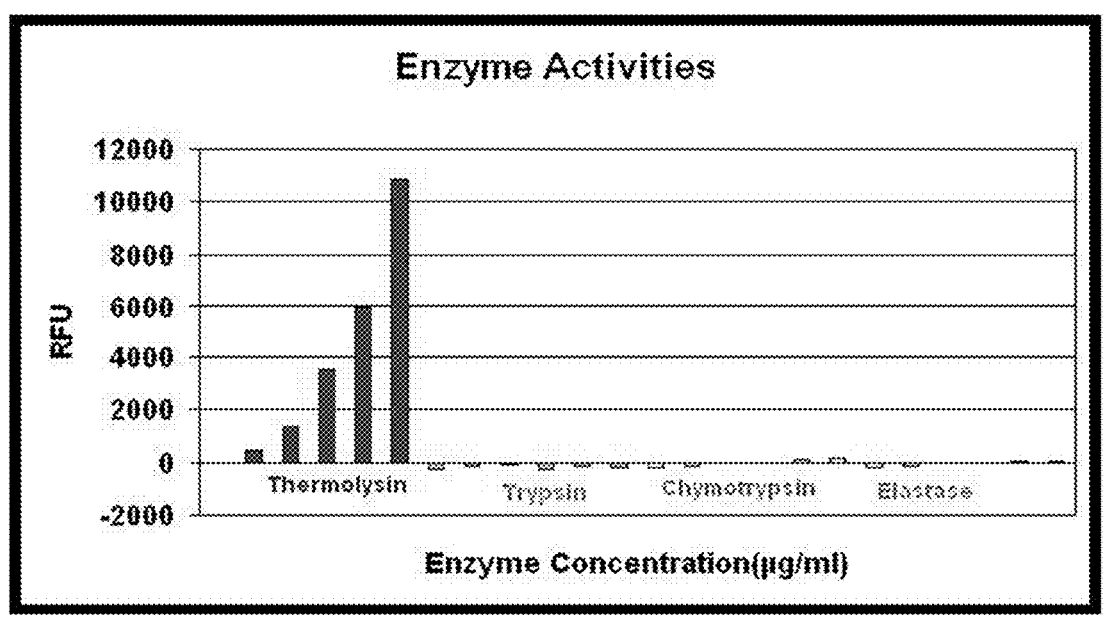
FIG. 11 illustrates a dose response curve of various concentrations of proteases (thermolysin, trypsin, chymotrypsin, and elastase) using 50 µM of the protease substrate 5FAMcollagenPPT. The concentrations used of the proteases from left to right were 0.3125 µg/mL, 0.625 µg/mL, 1.25 µg/mL, 2.5 µg/mL, 5.0 µg/mL, and 10 µg/mL. The substrate is highly specific for the bacterial protease, thermolysin, but not for mammalian pancreatic enzymes such as trypsin, chemotrypsin and elastase, which do not cleave the protease substrate.

The fluorogenic assay was also used to test cleavage of the protease substrate 5FAMcollagenPPT in the presence of different pancreatic proteases. As shown in FIG. 11, the mammalian proteases trypsin, chymotrypsin, and elastase do not cleave the protease substrate. Thus, the substrate is specific to bacterial collagenase and neutral proteases, and is not cleaved by mammalian pancreatic proteases.

Example 4: Analysis of Protease Substrate Cleavage Products

Currently, the only method of evaluating protease enzyme activity is by using the pancreas to test the potency of proteases to digest the pancreatic tissue. Although this has been relatively helpful for the progress of pancreas digestion, the procedure is expensive, lengthy, and challenging. Hence, the need for a simple and effective assay to evaluate and standardize enzyme activity is highly desirable to overcome these problems (Qi 2015).

The novel protease substrates provided herein may be used to help develop cocktails of multiple enzymes that are needed to overcome the variability of extracellular matrix (ECM) of the pancreata among different age groups. Adult pancreas has strong collagen bands and therefore it is a challenging process to digest these bands using Liberase MTF C/T Roche enzymes (Qi 2015). Digestion of pancreata from younger donors is also difficult because islets are not free from acinar cells resulting in embedded/mantled islets (Qi 2015; Szot 2009; Balamurugan 2006; Meier 2014). Therefore, Serva Collagenase NB1 and Neutral Protease are used for pancreas digestion to free the islets from younger donors.

The cleavage sites produced by various proteases were analyzed using the known sequence of the novel protease substrate 5FAMcollagenPPT. As provided herein, the cleavage sites were determined based on the results of mass spectrometric analysis of the protease substrate 5FAMcollagenPPT peptide fragments obtained from an enzymatic reaction with various enzymes tested.

Results

Cleavage of the novel fluorogenic protease substrate 5FAMcollagenPPT was further investigated using various proteases. After cleavage of the substrate by proteases, the resulting cleavage products of the protease substrate were specifically analyzed using matrix-assisted laser desorption/ionization (MALDI) mass spectrometry.

The proteases listed in Table 7 were tested for cleavage of the 5FAMcollagenPPT protease substrate in a time-dependent cleavage assay. Briefly, the reaction buffer for the assay contained Tris HCl (50 mM), NaCl (150 mM), $CaCl_2$, (10 mM), at pH 7.5. The peptide concentration in the reaction buffer was 10 μM and the protease concentration was 20 μg/mL. The fluorescence intensity of the sample was measured at 1, 5, and 24 hours using a Victor X2 multilabel plate reader (Perkin Elmer) (see FIG. 12).

TABLE 7

Various proteases tested in cleavage assay.

| Protease | Units | Company |
|---|---|---|
| Collagenase I Liq | 0.24 Wünsch/mg | ROCHE |
| Collagenase II Liq | 14 Wünsch/mg | ROCHE |
| Collagenase NB1 | 118.3 Wünsch U/mg | SERVA |
| Collagenase I/II | 134.55 Wünsch U/mg | ROCHE |
| Neutral Protease NB | 26.3 DMC U/mg | ROCHE |
| Thermolysin | 18426 U/mg | ROCHE |

Figure 12:
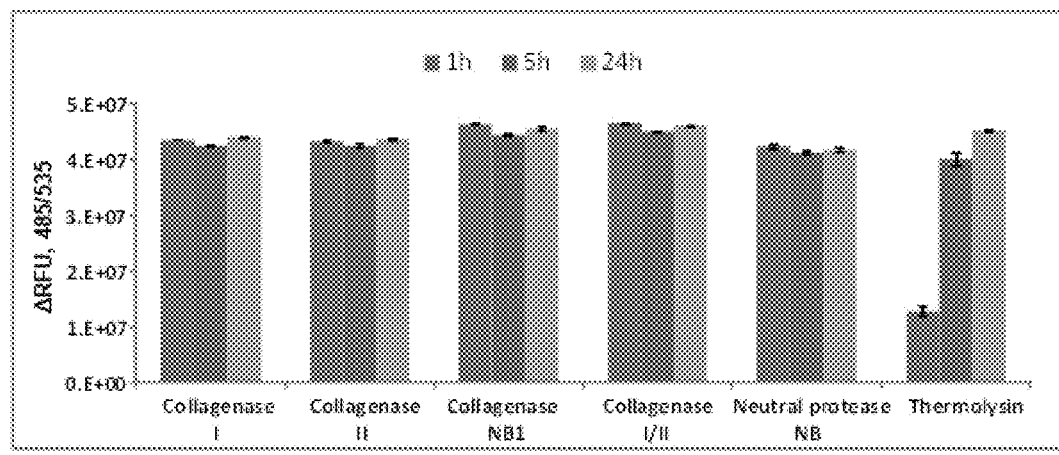
FIG. 12 shows data from a time dependent activity assay using various enzymes and the protease substrate 5FAMcollagenPPT. The proteases were incubated for 1 hour (left bars, medium grey), 5 hours (middle bars, dark grey), and 24 hours (right bars, light grey) with the protease substrate.

As shown in FIG. 12, almost all of the proteases tested, except for thermolysin, showed efficient cleavage of the protease substrate within the first hour of exposure to the protease substrate (see FIG. 12, 1 hour (left bar, medium grey)), and by the five hour time point, thermolysin had also sufficiently cleaved the substrate (see FIG. 12, 5 hour (middle bar, dark grey)).

Figure 13:
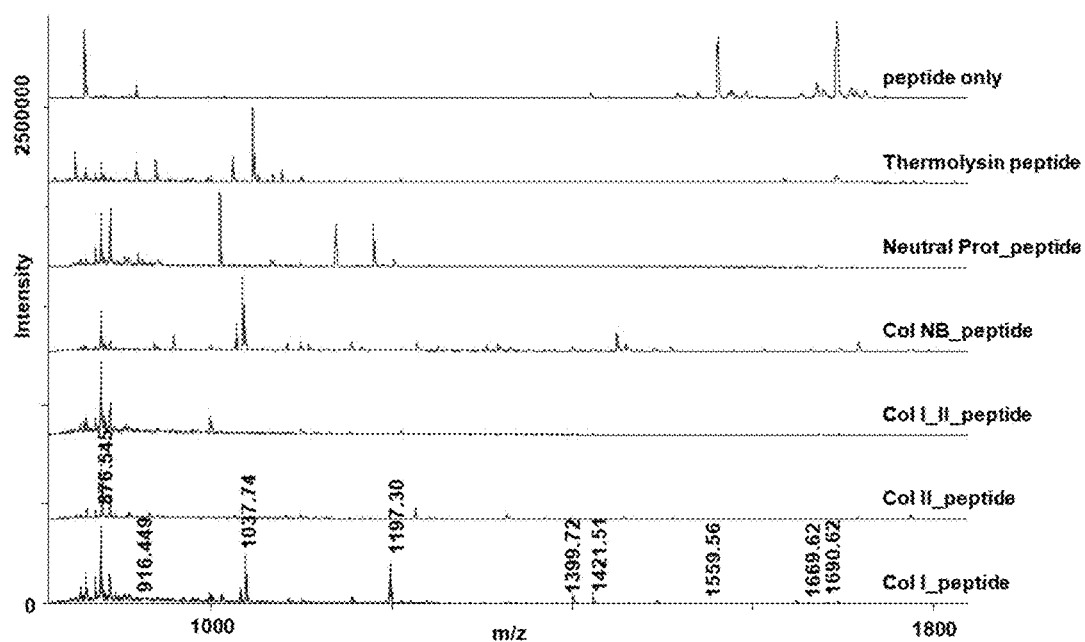
FIG. 13 shows matrix-assisted laser desorption/ionization (MALDI) spectra data of the full length protease substrate 5FAMcollagenPPT and the substrate cleavage products after incubation with the collagenase I, collagenase II, thermolysin, neutral protease NB, collagenase NB1, and collagenase I/II.

Next, the specific sequences of the protease substrate 5FAMcollagenPPT cleavage products were analyzed using MALDI. Briefly, each protease was incubated for 15 minutes with the protease substrate at 22° C. Buffer conditions and concentrations of the protease substrates and proteases were as described in Example 2. The uncleaved 5FAMcollagenPPT substrate has a molecular weight of 1669.8 Daltons. The molecular weights of the resulting products of the protease substrate after cleavage by various proteases are shown in Table 8 and FIG. 13.

TABLE 8

Cleavage products of the protease substrate 5FAMcollagenPPT.
5Fam-A1-G2-G3-P4-L5-G6-P7-P8-G9-P10-G11-G12-K13-[dabcyl],
uncleaved protease substrate, 1669.8 Da

| Sequence of collagenase peptide cleavage products | Col. I | Col. II | Therm. | NP NB | Col. NB1 | Col. I/II |
|---|---|---|---|---|---|---|
| | Peaks detected in the MALDI spectra, Da | | | | | |
| 5Fam-AGGP (N-term.) | | | 658.19 | 658.19 | | |
| 5Fam-AGGPL (N-term.) | 771.28 | 771.28 | 771.28 | 771.28 | | 771.28 |
| GPPGPGGK[dabcyl] (C-term.) | | | 916.47 | 916.47 | | |
| PPGPGGK[dabcyl] (C-term.) | | | | | | |
| 5Fam-AGGPLGPP (N-term.) | 1022.40 | 1022.40 | 1022.40 | 1022.40 | 1022.40 | 1022.40 |
| PLGPPGPGGK[dabcyl] (C-term.) | | | | | 1125.61 | |
| LGPPGPGGK[dabcyl] (C-term.) | | | 1028.56 | | 1028.56 | |

TABLE 8-continued

Cleavage products of the protease substrate 5FAMcollagenPPT.
5Fam-A1-G2-G3-P4-L5-G6-P7-P8-G9-P10-G11-G12-K13-[dabcyl],
uncleaved protease substrate, 1669.8 Da

| Sequence of collagenase peptide cleavage products | Proteases* | | | | | |
|---|---|---|---|---|---|---|
| | Col. I | Col. II | Therm. | NP NB | Col. NB1 | Col. I/II |
| | Peaks detected in the MALDI spectra, Da | | | | | |
| 5Fam-AGGPLGPPGPG (N-term.) | | | 1233.50 | | | |

*Col. I = Collagenase I; Col. II = Collagenase II; Therm. = Thermolysin; NP NB = Neutral Protease NB; Col. NB1 = Collagenase NB1; Col. I/II = Collagenase I/II The data indicate that each protease that was tested cleaved the protease substrate at more than one cleavage site on the substrate. Additionally, all of the proteases tested cleaved the protease substrate between the proline and glycine at amino acid positions 8 and 9 (see Table 4 and Table 8, sequence "5Fam-AGGPLGPP (N-term.)"). Additionally, almost all of the proteases tested (except for collagenase NB1) cleaved the protease substrate between the leucine and the glycine at positions 5 and 6 (see Table 4 and Table 8, sequence "5Fam-AGGPL (N-term.)").

Figure 14:
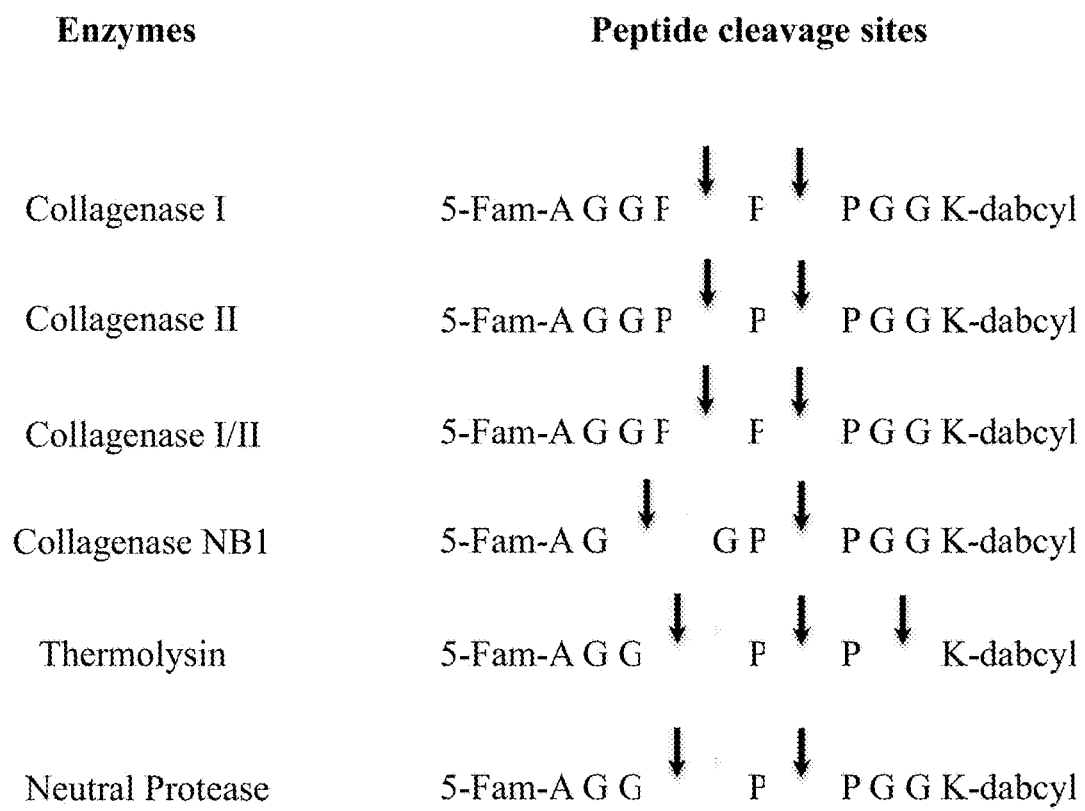
FIG. 14 shows the cleavage sites on the protease substrate 5FAMcollagenPPT when reacted with different enzymes.

As shown in FIG. 14 the results show that Roche Collagenase class I and II have similar cleavage sites on the peptide substrate, L↓G, and P↓G. However, Serva collagenase NB1 has three different cleavage sites: G↓P, P↓L, and P↓G. The neutral protease which is also produced by *Clostridium histolysticum* has three cleavage sites; P↓L, L↓G, and P↓G, while thermolysin prepared from different bacteria has four cleavage sites: P↓L, L↓G, P↓G, and G↓G. Interestingly, beside collagenase NB1, all other enzymes share same cleavage sites, P↓G and L↓G.

Example 5: Bioluminescent Protease Substrate

A bioluminescent protease substrate, thioredoxin-collagenPPT-SuperRenillaLuciferase, was developed for detection of protease cleavage activity. The polynucleotide and amino acid sequences of thioredoxin-collagenPPT-SuperRenillaLuciferase are presented as SEQ ID NO: 3 (FIG. 16) and SEQ ID NO: 4 (FIG. 17), respectively. As shown in detail in FIG. 18, the thioredoxin-collagenPPT-SuperRenillaLuciferase substrate is comprised of a fusion protein containing a thioredoxin tag, a serine-glycine linker, a polyhistidine tag, a serine-glycine linker, a thrombin cleavage site sequence, an S tag, an enterokinase cleavage site sequence, two repeating protease substrate sequences, and a Super *Renilla*-Luciferase sequence followed by a polyhistidine tag.

This bioluminescent protease substrate can be recombinantly expressed in *E. coli* and used in solution. The bioluminescent protease substrate can also be immobilized onto beads and used in a bead-based bioluminescent detection system to detect and/or measure the activity of bacterial proteases.

REFERENCES (1) Brennan, D. C.; Kopetskie, H. A.; Sayre, P. H.; Alejandro, R.; Cagliero, E.; Shapiro, A. M.; Goldstein, J. S.; DesMarais, M. R.; Booher, S.; Bianchine, P. J. Am. J. Transplant. 2015.

(2) Orr, C.; Stratton, J.; Rao, I.; Al-Sayed, M.; Smith, C.; El-Shahawy, M.; Dafoe, D.; Mullen, Y.; Al-Abdullah, I.; Kandeel, F. Cell Transplant. 2016, 25 (1), 83-95.

(3) Qi, M.; Kinzer, K.; Danielson, K. K.; Martellotto, J.; Barbaro, B.; Wang, Y.; Bui, J. T.; Gaba, R. C.; Knuttinen, G.; Garcia-Roca, R.; Tzvetanov, I.; Heitman, A.; Davis, M.; McGarrigle, J. J.; Benedetti, E.; Oberholzer, J. Acta Diabetol. 2014, 51 (5), 833-843.

(4) Balamurugan, A. N.; Naziruddin, B.; Lockridge, A.; Tiwari, M.; Loganathan, G.; Takita, M.; Matsumoto, S.; Papas, K.; Trieger, M.; Rainis, H.; Kin, T.; Kay, T. W.; Wease, S.; Messinger, S.; Ricordi, C.; Alejandro, R.; Markmann, J.; Kerr-Conti, J.; Rickels, M. R.; Liu, C.; Zhang, X.; Witkowski, P.; Posselt, A.; Maffi, P.; Secchi, A.; Berney, T.; O'Connell, P. J.; Hering, B. J.; Barton, F. B. Am. J. Transplant. 2014, 14 (11), 2595-2606.

(5) Kaddis, J. S.; Danobeitia, J. S.; Niland, J. C.; Stiller, T.; Fernandez, L. A. Am. J. Transplant. 2010, 10 (3), 646-656.

(6) Qi, M.; Valiente, L.; McFadden, B.; Omori, K.; Bilbao, S.; Juan, J.; Rawson, J.; Scott, S.; Ferreri, K.; Mullen, Y.; El-Shahawy, M.; Dafoe, D.; Kandeel, F.; Al-Abdullah, I. H. Transplant Direct 2015, 1 (4).

(7) Johnson, P. R.; White, S. A.; London, N. J. Cell Transplant. 1996, 5 (4), 437-452.

(8) Uscanga, L.; Kennedy, R. H.; Stocker, S.; Grimaud, J. A.; Sarles, H. Digestion 1984, 30 (3), 158-164.

(9) Kennedy, R. H.; Bockman, D. E.; Uscanga, L.; Choux, R.; Grimaud, J. A.; Sarles, H. Pancreas 1987, 2 (1), 61-72.

(10) Nano, R.; Clissi, B.; Melzi, R.; Calori, G.; Maffi, P.; Antonioli, B.; Marzorati, S.; Aldrighetti, L.; Freschi, M.; Grochowiecki, T.; Socci, C.; Secchi, A.; Di Carlo, V.; Bonifacio, E.; Bertuzzi, F. Diabetologia 2005, 48 (5), 906-912.

(11) Brandhorst, H.; Brandhorst, D.; Hesse, F.; Ambrosius, D.; Brendel, M.; Kawakami, Y.; Bretzel, R. G. Diabetes 2003, 52 (5), 1143-1146.

(12) Balamurugan, A.; Green, M.; Breite, A. G.; Loganathan, G.; Wilhelm, J. J.; Tweed, B.; Vargova, L.; Lockridge, A.; Kuriti, M.; Hughes, M.; Williams, S.; Hering, B.; Dwulet, F.; McCarthy, R. Transplant Direct 2015, 2 (1), e54.

(13) Linetsky, E.; Bottino, R.; Lehmann, R.; Alejandro, R.; Inverardi, L.; Ricordi, C. Diabetes 1997, 46 (7), 1120-1123.

(14) Kin, T.; O'Gorman, D.; Senior, P.; Shapiro, A. M. Islets 2010, 2 (5), 278-282.

(15) Fetterhoff, T. J.; Cavanagh, T. J.; Wile, K. J.; Wright, M. J.; Dwulet, F. E.; Gill, J.; Ellis, B.; Smith, M. E.; Critser, J. K.; Zieger, M.; et al. Transplant. Proc. 1995, 27 (6), 3282-3283.

(16) Linetsky, E.; Selvaggi, G.; Bottino, R.; Kong, S. S.; Qian, T.; Alejandro, R.; Ricordi, C. Transplant. Proc. 1995, 27 (6), 3264.

(17) Bucher, P.; Mathe, Z.; Bosco, D.; Andres, A.; Kurfuerst, M.; Ramsch-Gunther, N.; Buhler, L.; Morel, P.; Berney, T. Transplant. Proc. 2004, 36 (4), 1143-1144.

(18) Caballero-Corbalan, J.; Friberg, A. S.; Brandhorst, H.; Nilsson, B.; Andersson, H. H.; Felldin, M.; Foss, A.; Salmela, K.; Tibell, A.; Tufveson, G.; Korsgren, O.; Brandhorst, D. Transplantation 2009, 88 (12), 1400-1402.

(19) Szot, G. L.; Lee, M. R.; Tavakol, M. M.; Lang, J.; Dekovic, F.; Kerlan, R. K.; Stock, P. G.; Posselt, A. M. Transplantation 2009, 88 (6), 753-756.

(20) Yamamoto, T.; Ricordi, C.; Messinger, S.; Sakuma, Y.; Miki, A.; Rodriguez, R.; Haertter, R.; Khan, A.; Alejandro, R.; Ichii, H. Transplantation 2007, 84 (8), 997-1002.

(21) McCarthy, R. C.; Spurlin, B.; Wright, M. J.; Breite, A. G.; Sturdevant, L. K.; Dwulet, C. S.; Dwulet, F. E. Transplant. Proc. 2008, 40 (2), 339-342.

(22) Wunsch, E.; Heidrich, H. G. Hoppe Seylers Z. Physiol. Chem. 1963, 333, 149-151.

(23) Matsushita, O.; Jung, C. M.; Katayama, S.; Minami, J.; Takahashi, Y.; Okabe, A. J. Bacteriol. 1999, 181 (3), 923-933.

(24) Tokmina-Roszyk, M.; Tokmina-Roszyk, D.; Bhowmick, M.; Fields, G. B. Anal. Biochem. 2014, 453, 61-69.

(25) Saikumari, Y. K.; Balaram, P. Biopolymers 2008, 90 (2), 131-137.

(26) Salamone, M.; Seidita, G.; Cuttitta, A.; Rigogliuso, S.; Mazzola, S.; Bertuzzi, F.; Ghersi, G. Transplant. Proc. 2010, 42 (6), 2043-2048.

(27) Baici, A.; Cohen, G.; Fehr, K.; Boni, A. Anal. Biochem. 1980, 108 (2), 230-232.

(28) Kaplan, B. E.; Hefta, L. J.; Blake, R. C., 2nd; Swiderek, K. M.; Shively, J. E. J. Pept. Res. 1998, 52 (4), 249-260.

(29) Weimer, S.; Oertel, K.; Fuchsbauer, H. L. Anal. Biochem. 2006, 352 (1), 110-119.

(30) Cummings, R. T.; Salowe, S. P.; Cunningham, B. R.; Wiltsie, J.; Park, Y. W.; Sonatore, L. M.; Wisniewski, D.; Douglas, C. M.; Hermes, J. D.; Scolnick, E. M. Proc. Natl. Acad. Sci. U.S.A 2002, 99 (10), 6603-6606.

(31) Matayoshi, E. D.; Wang, G. T.; Krafft, G. A.; Erickson, J. Science 1990, 247 (4945), 954-958.

(32) Bagramyan, K.; Barash, J. R.; Arnon, S. S.; Kalkum, M. PLoS One 2008, 3 (4), e2041.

(33) Diaz, S. A.; Malonoski, A. P.; Susumu, K.; Hofele, R. V.; Oh, E.; Medintz, I. L. Anal Bioanal Chem 2015, 407 (24), 7307-7318.

(34) UniProt Knowledgebase http://www.uniprot.org/.

(35) Standard Protein BLAST http://blast.ncbi.nlm.nih.gov/Blast.cgi?PAGE=Proteins.

(36) Balamurugan, A. N.; Chang, Y.; Bertera, S.; Sands, A.; Shankar, V.; Trucco, M.; Bottino, R. Diabetologia 2006, 49 (8), 1845-1854.

(37) Meier, R. P.; Sert, I.; Morel, P.; Muller, Y. D.; Borot, S.; Badet, L.; Toso, C.; Bosco, D.; Berney, T. Transpl. Int. 2014, 27 (9), 949-955.

(38) Balamurugan, A. N.; He, J.; Guo, F.; Stolz, D. B.; Bertera, S.; Geng, X.; Ge, X.; Trucco, M.; Bottino, R. Am. J. Transplant. 2005, 5 (11), 2671-2681.

(39) Voss, E. W., Jr.; Workman, C. J.; Mummert, M. E. Biotechniques 1996, 20 (2), 286-291.

(40) Wu, Q.; Li, C.; Li, C.; Chen, H.; Shuliang, L. Appl. Biochem. Biotechnol. 160 (1), 129-139.

(41) Van Wart, H. E.; Steinbrink, D. R. Biochemistry 1985, 24 (23), 6520-6526.

(42) Brandhorst, H.; Raemsch-Guenther, N.; Raemsch, C.; Friedrich, O.; Huettler, S.; Kurfuerst, M.; Korsgren, O.; Brandhorst, D. Transplantation 2008, 85 (3), 456-461.

(43) Kin, T.; Zhai, X.; O'Gorman, D.; Shapiro, A. M. Transpl. Int. 2008, 21 (11), 1059-1065.

(44) U.S. Pat. No. 5,589,171 to Wegman, entitled "Treatment of Dupuytren's disease with collagenase," filed Aug. 22, 1994 and issued Dec. 31, 1996.

(45) Gray, D. W. R., et al., Diabetes 33(11):1055-1061 (1984).

What is claimed is:

1. A fluorogenic protease substrate comprising: (a) a donor fluorophore; (b) an acceptor having an absorbance spectrum overlapping the emission spectrum of the donor fluorophore; and (c) one or more amino acid sequences comprising at least one bacterial protease cleavage site, the amino acid sequence comprising:

Ala-Gly-Gly-Pro-Leu-Gly-Pro-Pro-Gly-Pro-Gly-Gly (i.e., SEQ ID NO: 1).

2. The fluorogenic protease substrate of claim 1, wherein the donor fluorophore is one or more fluorophores conjugated at or near the N-terminus of the protease substrate and the acceptor is a DABYCL conjugated at or near the C-terminus of the protease substrate.

3. The fluorogenic protease substrate of claim 2, wherein the fluorogenic protease substrate comprises:

[5-Fam]-Ala-Gly-Gly-Pro-Leu-Gly-Pro-Pro-Gly-Pro-

Gly-Gly-Lys-[DABYCL]-amide (i.e., SEQ ID NO: 2).

4. The fluorogenic protease substrate of claim 1, wherein the bacterial protease cleavage site is a collagenase cleavage site.

5. The fluorogenic protease substrate of claim 1, wherein the fluorogenic protease substrate is resistant to cleavage by trypsin, chymotrypsin and elastase.

6. A method for detecting the presence of one or more bacterial proteases in a sample comprising:

exposing the sample putatively containing the one or more bacterial proteases to an enrichment matrix comprising a fluorogenic protease substrate that is capable of eliciting a detectable fluorescence signal when modified by the one or more bacterial proteases, the fluorogenic protease substrate comprising one or more amino acid sequences comprising at least one bacterial protease cleavage site, the amino acid sequence comprising:

Ala-Gly-Gly-Pro-Leu-Gly-Pro-Pro-Gly-Pro-Gly-Gly (i.e., SEQ ID NO: 1);

measuring the level of change in the detectable fluorescence signal; and
detecting the presence of the one or more bacterial proteases when the level of change in the detectable fluorescence signal in the sample is elevated.

7. The method of claim 6, wherein the fluorogenic protease substrate comprises:

[5-Fam]-Ala-Gly-Gly-Pro-Leu-Gly-Pro-Pro-Gly-Pro-

Gly-Gly-Lys-[DABYCL]-amide (i.e., SEQ ID NO: 2).

8. The method of claim 7, wherein the one or more bacterial proteases are used for the preparation of islet cells.

9. The method of claim 7, wherein the one or more bacterial proteases are used for isolating primary cells or stem cells.

10. The method of claim 7, wherein the one or more bacterial proteases comprise one or more of class I collagenase, class II collagenase, thermolysin, neutral protease, and dispase.

11. The method of claim 7, wherein the enrichment matrix further comprises a protease substrate specific antibody that binds the fluorogenic protease substrate in the sample.

12. The method of claim 11, wherein the protease substrate specific antibody binds a region of the fluorogenic protease substrate wherein,
if the region of the fluorogenic protease substrate is a fluorophore, the antibody is an anti-fluorescein antibody;
if the region of the fluorogenic protease substrate is an acceptor, the antibody is an anti-DABYCL antibody; and
if the region of the fluorogenic protease substrate is one or more amino acids of the fluorogenic protease substrate amino acid sequence, the antibody is a sequence specific antibody.

13. The method of claim 6, wherein the fluorogenic protease substrate is resistant to cleavage by trypsin, chymotrypsin and elastase.

14. The method of claim 6, wherein the enrichment matrix is provided in one or more columns.

15. A bacterial protease detection kit comprising:
an enrichment matrix comprised of one or more fluorogenic protease substrates comprising: (a) a donor fluorophore; (b) an acceptor having an absorbance spectrum overlapping the emission spectrum of the donor fluorophore; and (c) one or more amino acid sequences comprising at least one bacterial protease cleavage site, the amino acid sequence comprising:

Ala-Gly-Gly-Pro-Leu-Gly-Pro-Pro-Gly-Pro-Gly-Gly (i.e., SEQ ID NO: 1), wherein a detectable fluorescence signal is produced upon interaction of the substrate with the bacterial protease.

16. The kit of claim 15, wherein the fluorogenic protease substrate comprises:

[5-Fam]-Ala-Gly-Gly-Pro-Leu-Gly-Pro-Pro-Gly-Pro-Gly-Gly-Lys-[DABYCL]-amide (i.e., SEQ ID NO: 2).

17. The kit of claim 15, wherein the bacterial protease comprises one or more of class I collagenase, class II collagenase, thermolysin, neutral protease, and dispase.

18. The kit of claim 15, wherein the enrichment matrix further comprises a fluorogenic substrate specific antibody that binds a region of the fluorogenic protease substrate in the sample.

19. The kit of claim 15, wherein:
if the region of the fluorogenic protease substrate is the fluorophore, the antibody is an anti-fluorescein antibody;
if the region of the fluorogenic protease substrate is the acceptor, the antibody is an anti-DABYCL antibody; and
if the region of the fluorogenic protease substrate is one or more amino acids of the fluorogenic protease substrate amino acid sequence, the antibody is a sequence-specific antibody.

20. The kit of claim 15, wherein the fluorogenic protease substrate is resistant to cleavage by trypsin, chymotrypsin and elastase.

21. A bioluminescent protease substrate comprising one or more luciferase proteins or fragments thereof and one or more amino acid sequences comprising at least one bacterial protease cleavage site, the amino acid sequence comprising:

Ala-Gly-Gly-Pro-Leu-Gly-Pro-Pro-Gly-Pro-Gly-Gly (i.e., SEQ ID NO: 1).

22. The bioluminescent protease substrate of claim 21, wherein the bioluminescent protease substrate further comprises one or more selected from a positive control cleavage site, an affinity tag, and a linker.

23. The bioluminescent protease substrate of claim 21, wherein the bioluminescent protease substrate comprises SEQ ID NO: 4.

24. The bioluminescent protease substrate of claim 21, wherein the bacterial protease cleavage site is one or more collagenase cleavage sites.

25. A method for detecting the presence of one or more bacterial proteases in a sample comprising:
exposing the sample putatively containing the one or more bacterial proteases to an enrichment matrix comprising a bioluminescent protease substrate that is capable of eliciting a detectable luminogenic signal when modified by the one or more bacterial proteases, the bioluminescent protease substrate comprising one or more luciferase proteins or fragments thereof and one or more amino acid sequences comprising at least one bacterial protease cleavage site, the amino acid sequence comprising:

Ala-Gly-Gly-Pro-Leu-Gly-Pro-Pro-Gly-Pro-Gly-Gly (i.e., SEQ ID NO: 1);

measuring the level of change in the detectable luminogenic signal; and
detecting the presence of the one or more bacterial proteases when the level of change in the detectable luminogenic signal in the sample is elevated.

26. The method of claim 25, wherein the bioluminescent protease substrate further comprises one or more selected from a positive control cleavage site, an affinity tag, and a linker.

27. The method of claim 26, wherein the bioluminescent protease substrate comprises SEQ ID NO: 4.

28. The method of claim 27, wherein the one or more bacterial proteases are used for the preparation of islet cells.

29. The method of claim 27, wherein the one or more bacterial proteases are used for isolating primary cells or stem cells.

30. The method of claim 27, wherein the one or more bacterial proteases comprise one or more of class I collagenase, class II collagenase, thermolysin, neutral protease, and dispase.

31. The method of claim 27, wherein the enrichment matrix further comprises a protease substrate specific antibody that binds the bioluminescent protease substrate in the sample.

32. The method of claim 27, wherein the enrichment matrix is provided in one or more columns.

33. A bacterial protease detection kit comprising:
an enrichment matrix comprising one or more bioluminescent protease substrates comprising one or more luciferase proteins or fragments thereof and one or more amino acid sequences comprising at least one bacterial protease cleavage site, the amino acid sequence comprising:

Ala-Gly-Gly-Pro-Leu-Gly-Pro-Pro-Gly-Pro-Gly-Gly (i.e., SEQ ID NO: 1), wherein a detectable fluorescence signal is produced upon interaction of the substrate with the bacterial protease.

34. The kit of claim 33, wherein the bioluminescent protease substrate further comprises one or more selected from a positive control cleavage site, an affinity tag, and a linker.

35. The kit of claim 33, wherein the bioluminescent protease substrate comprises SEQ ID NO: 4.

36. The kit of claim 33, wherein the bacterial protease comprises one or more of class I collagenase, class II collagenase, thermolysin, neutral protease, and dispase.

37. The kit of claim 33, wherein the enrichment matrix further comprises a protease substrate specific antibody that binds the bioluminescent protease substrate in the sample.

38. The kit of claim 33, wherein the enrichment matrix is provided in one or more columns.

* * * * *

SEQUENCE LISTING

```
<160> NUMBER OF SEQ ID NOS: 4

<210> SEQ ID NO 1
<211> LENGTH: 12
<212> TYPE: PRT
<213> ORGANISM: Artificial Sequence
<220> FEATURE:
<223> OTHER INFORMATION: protease substrate

<400> SEQUENCE: 1

Ala Gly Gly Pro Leu Gly Pro Pro Gly Pro Gly Gly
1               5                   10

<210> SEQ ID NO 2
<211> LENGTH: 13
<212> TYPE: PRT
<213> ORGANISM: Artificial Sequence
<220> FEATURE:
<223> OTHER INFORMATION: 5FAMcollagenPPT protease substrate

<400> SEQUENCE: 2

Ala Gly Gly Pro Leu Gly Pro Pro Gly Pro Gly Gly Lys
1               5                   10
```

<210> SEQ ID NO 3
<211> LENGTH: 1530
<212> TYPE: DNA
<213> ORGANISM: Artificial Sequence
<220> FEATURE:
<223> OTHER INFORMATION: thioredoxin-collagenPPT-SuperRenillaLuciferase bioluminescent protease substrate

<400> SEQUENCE: 3

| | | |
|---|---|---|
| atgagcgata aaattattca cctgactgac gacagttttg acacggatgt actcaaagcg | 60 |
| gacgggcga tcctcgtcga tttctgggca gagtggtgcg gtccgtgcaa aatgatcgcc | 120 |
| ccgattctgg atgaaatcgc tgacgaatat cagggcaaac tgaccgttgc aaaactgaac | 180 |
| atcgatcaaa accctggcac tgcgccgaaa tatggcatcc gtggtatccc gactctgctg | 240 |
| ctgttcaaaa acggtgaagt ggcggcaacc aaagtgggtg cactgtctaa aggtcagttg | 300 |
| aaagagttcc tcgacgctaa cctggccggt tctggttctg gccatatgca ccatcatcat | 360 |
| catcattctt ctggtctggt gccacgcggt tctggtatga agaaaccgc tgctgctaaa | 420 |
| ttcgaacgcc agcacatgga cagcccagat ctgggtaccg acgacgacga caaggccatg | 480 |
| gcgatatcgg atccgaattc ggccggtggt ccgctgggtc cgccgggtcc ggtggtgcc | 540 |
| ggtggtccgc tgggtccgcc gggtccgggt ggtaccagca agtttatga tccggaacag | 600 |
| cgtaaacgta tgattaccgg tccgcagtgg tgggcacgtt gtaaacaaat gaatgttctg | 660 |
| gactccttca tcaactatta cgatagcgaa aaacatgccg aaaacgccgt tattttctg | 720 |
| catggtaatg cagcaagcag ctatctgtgg cgtcatgttg ttccgcatat tgaaccggtt | 780 |
| gcccgttgta ttattccgga tctgattggt atgggtaaaa gcggtaaatc aggtaatggt | 840 |
| agctatcgtc tgctggatca ttacaaatat ctgaccgcat ggtttgaact gctgaatctg | 900 |
| ccgaaaaaaa tcatctttgt tggtcatgat tggggtgcat gtctggcatt tcattatagc | 960 |
| tatgaacacc aggacaaaat caaagccatt gttcatgcgg aaagcgttgt tgatgttatt | 1020 |
| gaaagctggg atgaatggcc tgatatcgaa gaagatattg ccctgattaa aagcgaagag | 1080 |
| ggtgaaaaaa tggtgctgga aaacaacttt tttgtggaaa ccgttctgcc gagcgttatt | 1140 |
| atgcgtaaac tggaaccgga agaatttgca gcatatctgg aaccgtttaa agaaaaaggt | 1200 |
| gaagttcgtc gtccgaccct gagctggctg cgtgaaattc cgctggttaa aggtggtaaa | 1260 |
| ccggatgttg ttcagattgt gcgtaactat aatgcatatc tgcgtgcaag tgatgacctg | 1320 |
| cctaaaatgt ttatcgaaag cgatccgggt ttttttagca acgcaattat tgagggtgcc | 1380 |
| aaaaaattcc cgaataccga atttgtgaaa gtgaaaggtc tgcactttag ccaagaggat | 1440 |
| gcaccggatg aaatgggcaa atatatcaaa agctttgtgg aacgcgtgct gaaaaatgaa | 1500 |
| cagctcgagc accaccacca ccaccactga | 1530 |

<210> SEQ ID NO 4
<211> LENGTH: 509
<212> TYPE: PRT
<213> ORGANISM: Artificial Sequence
<220> FEATURE:
<223> OTHER INFORMATION: thioredoxin-collagenPPT-SuperRenillaLuciferase bioluminescent protease substrate

<400> SEQUENCE: 4

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

```
Cys Gly Pro Cys Lys Met Ile Ala Pro Ile Leu Asp Glu Ile Ala Asp
            35                  40                  45

Glu Tyr Gln Gly Lys Leu Thr Val Ala Lys Leu Asn Ile Asp Gln Asn
 50                  55                  60

Pro Gly Thr Ala Pro Lys Tyr Gly Ile Arg Gly Ile Pro Thr Leu Leu
 65                  70                  75                  80

Leu Phe Lys Asn Gly Glu Val Ala Ala Thr Lys Val Gly Ala Leu Ser
                 85                  90                  95

Lys Gly Gln Leu Lys Glu Phe Leu Asp Ala Asn Leu Ala Gly Ser Gly
             100                 105                 110

Ser Gly His Met His His His His His His Ser Ser Gly Leu Val Pro
             115                 120                 125

Arg Gly Ser Gly Met Lys Glu Thr Ala Ala Ala Lys Phe Glu Arg Gln
             130                 135                 140

His Met Asp Ser Pro Asp Leu Gly Thr Asp Asp Asp Asp Lys Ala Met
145                 150                 155                 160

Ala Ile Ser Asp Pro Asn Ser Ala Gly Gly Pro Leu Gly Pro Pro Gly
                 165                 170                 175

Pro Gly Gly Ala Gly Gly Pro Leu Gly Pro Pro Gly Pro Gly Gly Thr
             180                 185                 190

Ser Lys Val Tyr Asp Pro Glu Gln Arg Lys Arg Met Ile Thr Gly Pro
             195                 200                 205

Gln Trp Trp Ala Arg Cys Lys Gln Met Asn Val Leu Asp Ser Phe Ile
             210                 215                 220

Asn Tyr Tyr Asp Ser Glu Lys His Ala Glu Asn Ala Val Ile Phe Leu
225                 230                 235                 240

His Gly Asn Ala Ala Ser Ser Tyr Leu Trp Arg His Val Val Pro His
                 245                 250                 255

Ile Glu Pro Val Ala Arg Cys Ile Ile Pro Asp Leu Ile Gly Met Gly
             260                 265                 270

Lys Ser Gly Lys Ser Gly Asn Gly Ser Tyr Arg Leu Leu Asp His Tyr
             275                 280                 285

Lys Tyr Leu Thr Ala Trp Phe Glu Leu Leu Asn Leu Pro Lys Lys Ile
             290                 295                 300

Ile Phe Val Gly His Asp Trp Gly Ala Cys Leu Ala Phe His Tyr Ser
305                 310                 315                 320

Tyr Glu His Gln Asp Lys Ile Lys Ala Ile Val His Ala Glu Ser Val
                 325                 330                 335

Val Asp Val Ile Glu Ser Trp Asp Glu Trp Pro Asp Ile Glu Glu Asp
             340                 345                 350

Ile Ala Leu Ile Lys Ser Glu Glu Gly Glu Lys Met Val Leu Glu Asn
             355                 360                 365

Asn Phe Phe Val Glu Thr Val Leu Pro Ser Val Ile Met Arg Lys Leu
             370                 375                 380

Glu Pro Glu Glu Phe Ala Ala Tyr Leu Glu Pro Phe Lys Glu Lys Gly
385                 390                 395                 400

Glu Val Arg Arg Pro Thr Leu Ser Trp Leu Arg Glu Ile Pro Leu Val
                 405                 410                 415

Lys Gly Gly Lys Pro Asp Val Val Gln Ile Val Arg Asn Tyr Asn Ala
             420                 425                 430

Tyr Leu Arg Ala Ser Asp Asp Leu Pro Lys Met Phe Ile Glu Ser Asp
             435                 440                 445

Pro Gly Phe Phe Ser Asn Ala Ile Ile Glu Gly Ala Lys Lys Phe Pro
```

```
               450                 455                 460
Asn Thr Glu Phe Val Lys Val Lys Gly Leu His Phe Ser Gln Glu Asp
465                 470                 475                 480

Ala Pro Asp Glu Met Gly Lys Tyr Ile Lys Ser Phe Val Glu Arg Val
                485                 490                 495

Leu Lys Asn Glu Gln Leu Glu His His His His His His
                500                 505
```